(12) United States Patent
Michel et al.

(10) Patent No.: US 7,087,596 B2
(45) Date of Patent: Aug. 8, 2006

(54) 2-OXO-PIPERIDINYL- AND 2-OXO-AZEPANYL ALKANOIC ACID DERIVATIVES FOR THE TREATMENT OF EPILEPSY AND OTHER NEUROLOGICAL DISORDERS

(75) Inventors: Philippe Michel, Beersel (BE); Benoît Kenda, Emines (BE)

(73) Assignee: UCB, S.A., Brussels (BE)

( * ) Notice: Subject to any disclaimer, the term of this patent is extended or adjusted under 35 U.S.C. 154(b) by 1 day.

(21) Appl. No.: 10/476,791

(22) PCT Filed: May 17, 2003

(86) PCT No.: PCT/EP02/05503

§ 371 (c)(1),
(2), (4) Date: Nov. 6, 2003

(87) PCT Pub. No.: WO02/094787

PCT Pub. Date: Nov. 28, 2002

(65) Prior Publication Data
US 2004/0132717 A1 Jul. 8, 2004

(30) Foreign Application Priority Data
May 23, 2001 (EP) .................................. 01112541

(51) Int. Cl.
*A61K 31/55* (2006.01)
*C07D 223/04* (2006.01)
(52) U.S. Cl. .................................. 514/212.03; 540/485
(58) Field of Classification Search ............... 540/485; 514/212.03
See application file for complete search history.

(56) References Cited

U.S. PATENT DOCUMENTS

| 5,334,720 A | 8/1994 | Schmiesing et al. |
| 5,719,296 A | 2/1998 | Acton, III et al. |
| 5,776,950 A | 7/1998 | Lee et al. |

FOREIGN PATENT DOCUMENTS

| EP | 0 046 291 | 2/1982 |
| EP | 0 365 992 | 5/1990 |
| EP | 0 783 002 | 7/1997 |
| GB | 1 309 692 | 3/1973 |
| WO | 95 35308 | 12/1995 |
| WO | 01 19795 | 3/2001 |

OTHER PUBLICATIONS

Piro, J. et al, Tetrahedron Letters, 42(5), pp. 871-873 (2001).
Estiarte, M.A. et al., Tetrahedron, 55(33), pp. 10173-10186 (1999).
Dutton, F.E. et al., Tetrahedron Letters, 39(30), pp. 5313-5316, (1998).
Robl, J.A. et al., Journal of Medicinal Chemistry, 39(2), pp. 494-502, (1996).
Robl, J.A. et al, J. Am. Chem. Soc., 116(6), pp. 2348-2355 (1994).
Depriest, S.A., et al, J. Am. Chem. Soc., 115(13), pp. 5372-5384 (1993).
De Laszlo, S.E. et al., J. Med. Chem., 35(5), pp. 833-846 (1992).
Aebi, J.D. et al., J. Med. Chem., 31(9), pp. 1805-1815 (1988).
Milewska M.J. et al., Synthesis, 12, pp. 1485-1488 (1996).
Prous, Drugs of the Future, 19(2), pp. 111-113 (1994).
Angelucci, L. et al., J. Med. Chem, 36(11), pp. 1511-1519 (1993).
Sreenivasan, U. et al., J. Med. Chem., 36(2), pp. 256-263 (1993).
Micouin L. et al., Tetrahedron, 52(22), pp. 7719-7726, (1996).

*Primary Examiner*—Rita Desai
(74) *Attorney, Agent, or Firm*—Wenderoth, Lind & Ponack, L.L.P.

(57) ABSTRACT

This invention relates to new 2-oxo-piperidinyl- and 2-oxo-azepanyl alkanoic acid derivatives of formula (1) having anticonvulsant activity which are useful as therapeutic agents for the treatment or prevention of epilepsy and other neurological disorders. The invention also concerns processes for preparing these derivatives and novel intermediates used in the preparation of these derivatives.

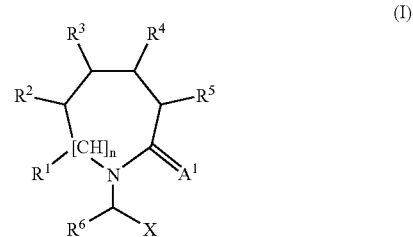

21 Claims, No Drawings

2-OXO-PIPERIDINYL- AND 2-OXO-AZEPANYL ALKANOIC ACID DERIVATIVES FOR THE TREATMENT OF EPILEPSY AND OTHER NEUROLOGICAL DISORDERS

FIELD OF THE INVENTION

This invention relates to new 2-oxo-piperidinyl- and 2-oxo-azepanyl alkanoic acid derivatives having anticonvulsant activity which are useful as therapeutic agents for the treatment and/or prevention of epilepsy and other neurological disorders. The invention also concerns processes for preparing these derivatives and novel intermediates used in the preparation of these derivatives.

BACKGROUND OF THE INVENTION

Epilepsy is a relatively common neurological condition affecting 0.4–1% of the world's population (45–100 million people). For the general population there are approximately 20–70 new cases per 100,000 diagnosed each year with a 3–5% lifetime probability of developing the disease. The older established antiepileptic drugs (AEDs) phenyloin, carbamazepine, clonazepam, ethosuximide, valproic acid and barbiturates are widely prescribed but suffer from a range of side effects. Furthermore, there is a significant group of patients (20–30%) that are resistant to the currently available therapeutic agents. Since 1989 several new drugs have been launched, including felbamate, gabapentin, lamotrigine, oxcarbazepine, tiagabine, topimarate, vigabatrin, zonisamide and levetiracetam. While many of the new AEDs show improved efficacies and side-effect profiles, patients with intractable epilepsy remain untreated. There is clearly a need for improved medications (Cosford N. D. P. et al., Annual Reports in Medicinal Chemistry (1998), 33, 61–70).

U.S. Pat. No. 6,066,666 reports lactam and thiolactam derivatives having useful anticonvulsant and anxiolytic activity, and thus being effective in the treatment of epilepsy.

U.S. Pat. No. 5,334,720 relates to diphenyl-1-(aminoalkyl)-2-piperidone and -2-pyrrolidinone derivatives, which possess anticonvulsant properties and are useful antiepileptic agents.

European Patent No. 0 162 036 B1 discloses levetiracetam or (S)-(−)-α-ethyl-2-oxo-1-pyrrolidineacetamide as well as its use as a protective agent for the treatment and the prevention of hypoxic and ischemic type aggressions of the central nervous system. This compound is also effective in the treatment of epilepsy, a therapeutic indication for which it has been demonstrated that its dextrorotatory enantiomer (R)-(+)-α-ethyl-2-oxo-1-pyrrolidineacetamide completely lacks activity (Gower A. J. et al., Eur. J. Pharmacol. (1992), 222, 193–203). In the European Patent No. 0 645 139 B1, levetiracetam has been disclosed for its anxiolytic activity. International Patent Application No. PCT/EP00/11808 discloses the use of levetiracetam for the curative and/or prophylactic treatment of bipolar disorders, migraine, chronic or neuropathic pain as well as combinations of levetiracetam with at least one compound inducing neural inhibition mediated by $GABA_A$ receptors.

Continuing its research work in the field of the treatment of epilepsy, the applicant discloses now new 2-oxo-piperidinyl- and 2-oxo-azepanyl alkanoic acid derivatives. These new 2-oxo-piperidinyl- and 2-oxo-azepanyl alkanoic acid derivatives are useful for the prevention or the treatment of epilepsy, epileptogenesis, seizure disorders and convulsions.

These compounds may also be used for the treatment of other neurological disorders including bipolar disorders, mania, depression, anxiety, migraine, trigeminal and other neuralgia, chronic pain, neuropathic pain, cerebral ischemia, cardiac arrhythmia, myotonia, cocaine abuse, stroke, myoclonus, essential tremor and other movement disorders, neonatal cerebral haemorrhage, amyotrophic lateral sclerosis, spasticity, Parkinson's disease and other degenerative diseases.

In addition the compounds according to the invention may be used in the treatment of bronchial asthma, asthmatic status and allergic bronchitis, asthmatic syndrome, bronchial hyperreactivity and bronchospastic syndromes as well as allergic and vasomotor rhinitis and rhinoconjunctivitis.

DESCRIPTION OF THE INVENTION

This invention provides novel compounds of the formula I

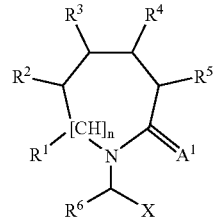

wherein n represents 0 or 1 whereby $R^1$ is not existent when n=0 and $R^1$ is existent when n=1;

$A^1$ represents an oxygen or a sulfur atom;

X is —$CONR^7R^8$, —$COOR^9$, —CO—$R^{10}$ or CN;

$R^1$ when existent, $R^2$, $R^3$, $R^4$ and $R^5$ are the same or different and each is independently hydrogen, halogen, hydroxy, thiol, amino, nitro, nitrooxy, cyano, azido, carboxy, amido, sulfonic acid, sulfonamide, alkyl, alkenyl, alkynyl, ester, ether, aryl, heterocycle, or an oxy derivative, thio derivative, amino derivative, acyl derivative, sulfonyl derivative or sulfinyl derivative, provided that at least one of the substituents R chosen from $R^1$ when existent, $R^2$, $R^3$, $R^4$ or $R^5$ is not hydrogen;

$R^6$ is hydrogen, alkyl, aryl or —$CH_2$—$R^{6a}$ wherein $R^{6a}$ is aryl, heterocycle, halogen, hydroxy, amino, nitro or cyano;

$R^7$, $R^8$ and $R^9$ are the same or different and each is independently hydrogen, hydroxy, alkyl, aryl, heterocycle or an oxy derivative; and $R^{10}$ is hydrogen, hydroxy, thiol, halogen, alkyl, aryl, heterocycle or a thio derivative;

their pharmaceutically acceptable salts, geometrical isomers (including cis and trans, Z and E isomers), enantiomers, diastereoisomers and mixtures thereof (including all possible mixtures of stereoisomers).

In the above formula, at least one substituent $R^1$ to $R^5$ is different from hydrogen. Some non-substituted compounds are disclosed in U.S. Pat. Nos. 5,468,733 and 5,516,759. U.S. Pat. No. 5,468,733 discloses non-ring substituted 2-oxo-1-pyrrolidinyl and 2-oxo-1-piperidinyl derivatives as inhibitors of the oncogene Ras protein. In particular, these compounds block the ability of Ras to transform normal cells to cancer cells, and therefore can be included in several chemotherapeutic compositions for treating cancer.

U.S. Pat. No. 5,516,759 discloses non-ring substituted 2-oxo-1-pyrrolidinyl, 2-oxo-1-piperidinyl and azepanyl derivatives present at the N-terminus of dodecapeptides possessing LHRH (luteinizing hormone-releasing hormone) antagonistic activity. Such LHRH antagonists are useful in the treatment of a variety of conditions in which suppression of sex steroids plays a key role including contraception, delay of puberty, treatment of benign prostatic hyperplasia a.o.

In the definitions set forth below, unless otherwise stated, $R^{11}$ and $R^{12}$ are the same or different and each is independently amido, alkyl, alkenyl, alkynyl, acyl, ester, ether, aryl, aralkyl, heterocycle or an oxy derivative, thio derivative, acyl derivative, amino derivative, sulfonyl derivative, or sulfinyl derivative, each optionally substituted with any suitable group, including, but not limited to, one or more moieties selected from lower alkyl or other groups as described below as substituents for alkyl.

The term "oxy derivative", as used herein, is defined as including —O—$R^{11}$ groups wherein $R^{11}$ is as defined above except for "oxy derivative". Non-limiting examples are alkoxy, alkenyloxy, alkynyloxy, acyloxy, oxyester, oxyamido, alkylsulfonyloxy, alkylsulfinyloxy, arylsulfonyloxy, arylsulfinyloxy, aryloxy, aralkoxy or heterocyclooxy such as pentyloxy, allyloxy, methoxy, ethoxy, phenoxy, benzyloxy, 2-naphthyloxy, 2-pyridyloxy, methylenedioxy, carbonate.

The term "thio derivative", as used herein, is defined as including —S—$R^{11}$ groups wherein $R^{11}$ is as defined above except for "thio derivative". Non-limiting examples are alkylthio, alkenylthio, alkynylthio and arylthio.

The term "amino derivative", as used herein, is defined as including —NHR$^{11}$ or —NR$^{11}$R$^{12}$ groups wherein $R^{11}$ and $R^{12}$ are as defined above. Non-limiting examples are mono- or di-alkyl-, alkenyl-, alkynyl- and arylamino or mixed amino.

The term "acyl derivative", as used herein, represents a radical derived from carboxylic acid and thus is defined as including groups of the formula $R^1$—CO—, wherein $R^{11}$ is as defined above and may also be hydrogen. Preferred are acyl derivatives of formula —COR$^{11}$ wherein $R^{11}$ is selected from hydrogen, C1–12 alkyl, C2–12 alkenyl, C2–12 alkenyl, heterocycle and aryl. Non-limiting examples are formyl, acetyl, propionyl, isobutyryl, valeryl, lauroyl, heptanedioyl, cyclohexanecarbonyl, crotonoyl, fumaroyl, acryloyl, benzoyl, naphthoyl, furoyl, nicotinoyl, 4-carboxybutanoyl, oxalyl, ethoxalyl, cysteinyl, oxamoyl.

The term "sulfonyl derivative", as used herein, is defined as including a group of the formula —SO$_2$—$R^{11}$, wherein $R^{11}$ is as defined above except for "sulfonyl derivative". Non-limiting examples are alkylsulfonyl, alkenylsulfonyl, alkynylsulfonyl and arylsulfonyl.

The term "sulfinyl derivative", as used herein, is defined as including a group of the formula —SO—$R^{11}$, wherein $R^{11}$ is as defined above except for "sulfinyl derivative". Non-limiting examples are alkylsulfinyl, alkenylsulfinyl, alkynylsulfinyl and arylsulfinyl.

The term "alkyl", as used herein, is defined as including saturated, monovalent hydrocarbon radicals having straight, branched or cyclic moieties or combinations thereof and generally containing 1–20 carbon atoms, most often 1 to 12 carbon atoms, preferably 1–7 carbon atoms for non-cyclic alkyl and 3–7 carbon atoms for cycloalkyl (in these two preferred cases, unless otherwise specified, "lower alkyl"), each optionally substituted by, preferably 1 to 5, substituents independently selected from the group consisting of halogen, hydroxy, thiol, amino, nitro, cyano, thiocyanato, acyl, acyloxy, sulfonyl derivative, sulfinyl derivative, alkylamino, carboxy, ester, ether, amido, azido, cycloalkyl, sulfonic acid, sulfonamide, thio derivative, alkylthio, oxyester, oxyamido, heterocycle, vinyl, alkoxy (preferably C1–5), aryloxy (preferably C6–10) and aryl(preferably C6–10).

Preferred are alkyl groups containing 1 to 7 carbon atoms, each optionally substituted by one or more substituents selected from hydroxy, halogen, cyano, thiocyanato, alkoxy, azido, alkylthio, cyclopropyl, acyl and phenyl. Most preferred are C1–4 alkyl and C3–7 cycloalkyl, each optionally substituted by one or more hydroxy, halogen, lower alkyl or/and azido.

Most preferred alkyl groups are hydroxymethyl, propyl, butyl, 2,2,2-trifluoroethyl, 2-bromo-2,2-difluoroethyl, 2-chloro-2,2-difluoroethyl, 3,3,3-trifluoropropyl, cyclopropylmethyl, iodomethyl, azidomethyl, 2,2-difluoropropyl, 2-iodo-2,2-difluoroethyl.

The term "lower alkyl", as used herein, and unless otherwise specified, refers to $C_1$ to $C_7$ saturated straight, branched or cyclic hydrocarbon. Non limiting examples are methyl, ethyl, propyl, isopropyl, butyl, tertiobutyl, pentyl, cyclopropyl, cyclopentyl, isopentyl, neopentyl, hexyl, isohexyl, cyclohexyl, 3-methypentyl, 2,2-dimethylbutyl, optionally substituted with any suitable group, including but not limited to one or more moieties selected from groups as described above for the alkyl groups. Preferably, lower alkyl is methyl.

The term "alkenyl", as used herein, is defined as including both branched and unbranched, unsaturated hydrocarbon radicals having at least one double bond, and being optionally substituted by at least one substituent selected from the group consisting of halogen, hydroxy, thiol, amino, thiocyanato, azido, alkylthio, cycloalkyl, acyl, nitro, cyano, aryl and heterocycle.

Prefered alkenyl groups are C2–C12 alkenyls, especially C2–6 alkenyls, such as ethenyl (=vinyl), 1-methyl-1-ethenyl, 2,2-dimethyl-1-ethenyl, 1-propenyl, 2-propenyl (=allyl), 1-butenyl, 2-butenyl, 3-butenyl, 4-pentenyl, 1-methyl-4-pentenyl, 3-methyl-1-pentenyl, 1-hexenyl, 2-hexenyl and the like, optionally being substituted by one or more substituents selected from halogen, cyano, thiocyanato, azido, alkylthio, cycloalkyl, phenyl and acyl. Most prefered is vinyl, optionally substituted by one or more halogen or/and lower alkyl, and especially 2,2-difluorovinyl, 2,2-dibromovinyl and 2,2-dichlorovinyl.

The term "alkynyl" as used herein, is defined as including a monovalent branched or unbranched hydrocarbon radical containing at least one carbon-carbon triple bond, for example ethynyl, 2-propynyl (=propargyl), and the like, and being optionally substituted by at least one substituent selected from the group consisting of halogen, hydroxy, thiol, amino, nitro, cyano, aryl, heterocycle, thiocyanato, azido, alkylthio, alkyl and acyl.

Preferred alkynyl groups are C2–12 alkyl, especially C2–6 alkynyl, optionally being substituted by one or more substituents selected from halogen, cyano, thiocyanato, azido, alkylthio, acyl, aryl such as phenyl and alkyl, preferably cycloalkyl.

Most preferred are ethynyl, propynyl and butynyl, optionally substituted by lower alkyl or/and halogen, and especially 1-propynyl, cyclopropylethynyl, 3-methyl-1-butynyl and 3,3,3-trifluoro-1-propynyl.

When present as bridging groups, alkyl, alkenyl and alkynyl represent straight- or branched chains, C1–12, preferably C1–4-alkylene or C2–12-, preferably C2–4-alkenylene or -alkynylene moieties respectively.

Groups where branched derivatives are conventionally qualified by prefixes such as "n", "sec", "iso" and the like (e.g. "n-propyl", "sec-butyl") are in the n-form unless otherwise stated.

The term "aryl", as used herein, is defined as including an organic radical derived from an aromatic hydrocarbon consisting of at least one ring, most often 1 to 3 rings and generally containing 6–30 carbon atoms by removal of one hydrogen, such as phenyl and naphthyl, each optionally substituted by one or more substituents independently selected from halogen, hydroxy, thiol, amino, nitro, cyano, acyl, acyloxy, sulfonyl, sulfinyl, alkylamino, carboxy, ester, ether, amido, azido, sulfonic acid, sulfonamide, alkylsulfonyl, alkylsulfinyl, C1–6-alkylthio, oxyester, oxyamido, aryl, C1–6-alkoxy, C6–10-aryloxy, C1–6-alkyl, C1–6-haloalkyl. Aryl radicals are preferably monocyclic or bicyclic containing 6–10 carbon atoms. Preferred aryl groups are phenyl and naphthyl each optionally substituted by one or more substituents independently selected from halogen, nitro, amino, azido, C1–6-alkoxy, C1–6-alkyl, C1–6-haloalkyl, sulfonyl and phenyl.

Preferred aryl is phenyl, optionally substituted by one or more halogen, lower alkyl, azido or nitro, such as 3-chlorophenyl and 3-azidophenyl.

The term "halogen", as used herein, includes an atom of Cl, Br, F, I.

The term "hydroxy", as used herein, represents a group of the formula —OH.

The term "thiol", as used herein, represents a group of the formula —SH.

The term "cyano", as used herein, represents a group of the formula —CN.

The term "nitro", as used herein, represents a group of the formula —$NO_2$.

The term "nitrooxy", as used herein, represents a group of the formula —$ONO_2$.

The term "amino", as used herein, represents a group of the formula —$NH_2$.

The term "azido", as used herein, represents a group of the formula —$N_3$.

The term "carboxy", as used herein, represents a group of the formula —COOH.

The term "sulfonic acid", as used herein, represents a group of the formula —$SO_3H$.

The term "sulfonamide", as used herein, represents a group of the formula —$SO_2NH_2$.

The term "ester", as used herein, is defined as including a group of formula —COO—$R^{11}$ wherein $R^{11}$ is as defined above except oxy derivative, thio derivative or amino derivative. Preferred are esters of formula —$COOR^1$ wherein $R^{11}$ is selected from C1–12 alkyl, C2–12 alkenyl, C2–12 alkynyl and aryl. Most preferred are esters where $R^{11}$ is a lower alkyl, especially methyl.

The term "ether" is defined as including a group selected from C1–50-straight or branched alkyl, or C2–50-straight or branched alkenyl or alkynyl groups or a combination of the same, interrupted by one or more oxygen atoms.

The term "amido" is defined as including a group of formula —$CONH_2$ or —$CONHR^{11}$ or —$CONR^{11}R^{12}$ wherein $R^{11}$ and $R^{12}$ are as defined above.

The term "heterocycle", as used herein, is defined as including an aromatic or non aromatic cyclic alkyl, alkenyl, or alkynyl moiety as defined above, having at least one O, S and/or N atom interrupting the carbocyclic ring structure and optionally, one of the carbon of the carbocyclic ring structure may be replaced by a carbonyl, and optionally being substituted with any suitable group, including but not limited to one or more moieties selected from lower alkyl, or other groups as described above for the alkyl groups. Non-limiting examples of heterocycles are pyridyl, furyl, pyrrolyl, thienyl, isothiazolyl, triazolyl, imidazolyl, benzimidazolyl, tetrazolyl, quinazolinyl, quinolizinyl, naphthyridinyl, pyridazinyl, pyrimidinyl, pyrazinyl, quinolyl, isoquinolyl, isobenzofuranyl, benzothienyl, pyrazolyl, indolyl, indolizinyl, purinyl, isoindolyl, carbazolyl, thiazolyl, 1,2,4-thiadiazolyl, thiomorpholinyl, thieno(2,3-b)furanyl, furopyranyl, benzofuranyl, benzoxepinyl, isooxazolyl, oxazolyl, thianthrenyl, benzothiazolyl, or benzoxazolyl, cinnolinyl, phthalazinyl, quinoxalinyl, 1-oxidopyridyl, phenanthridinyl, acridinyl, perimidinyl, phenanthrolinyl, phenothiazinyl, furazanyl, benzodioxolyl, isochromanyl, indolinyl, xanthenyl, hypoxanthinyl, pteridinyl, 5-azacytidinyl, 5-azauracilyl, triazolopyridinyl, imidazolopyridinyl, pyrrolopyrimidinyl, pyrazolopyrimidinyl, tetrahydrofuranyl, tetrahydropyranyl, piperidinyl, piperidyl, piperazinyl, imidazolidinyl, morpholino, morpholinyl, 1-oxaspiro(4.5)dec-2-yl, pyrrolidinyl, 2-oxo-pyrrolidinyl, sugar moieties (i.e. glucose, pentose, hexose, ribose, fructose, which may also be substituted) optionally substituted by alkyl or as described above for the alkyl groups. The term "heterocycle" also includes bicyclic, tricyclic and tetracyclic, spiro groups in which any of the above heterocyclic rings is fused to one or two rings independently selected from an aryl ring, a cyclohexane ring, a cyclohexene ring, a cyclopentane ring, a cyclopentene ring or another monocyclic heterocyclic ring or where a monocyclic heterocyclic group is bridged by an alkylene group, such as quinuclidinyl, 7-azabicyclo(2.2.1)heptanyl, 7-oxabicyclo(2.2.1)heptanyl, 8-azabicyclo(3.2.1)octanyl. The heterocycle is preferably selected from triazolyl, tetrazolyl, pyrrolidinyl, pyridyl, 1-oxidopyridyl, thiomorpholinyl, benzodioxolyl, furyl, oxazolyl, pyrimidinyl, pyrrolyl, thiadiazolyl, thiazolyl, thienyl and piperazinyl, each optionally substituted by one or more substituents selected from halogen, alkyl, substituted alkyl, alkoxy, nitro, amino, acyl and phenyl. More preferably the heterocycle is selected from tetrazolyl, pyrrolidinyl, pyridyl, furyl, pyrrolyl, thiazolyl and thienyl, each optionally substituted by one or more substituents selected from halogen, alkyl, halogen substituted alkyl, acyl, alkoxy, nitro, amino and phenyl, and especially from 2- and 3-thienyl, optionally substituted by one or more halogen, acyl such as formyl, cyano and/or lower alkyl, such as methyl.

In the above definitions it is to be understood that when a substituent such as $R^1$, $R^2$, $R^3$, $R^4$, $R^5$, $R^7$, $R^8$, $R^9$, $R^{10}$ is attached to the rest of the molecule via a heteroatom or a carbonyl, a straight- or branched chain, C1–12-, preferably C1–4-alkylene or C2–12, preferably C2–4-alkenylene or -alkynylene bridge may optionally be interposed between the heteroatom or the carbonyl and the point of attachment to the rest of the molecule.

The "pharmaceutically acceptable salts" according to the invention include therapeutically active, non-toxic base and acid salt forms which the compounds of formula (I) are able to form.

The acid addition salt form of a compound of formula (I) that occurs in its free form as a base can be obtained by treating said free base form with an appropriate acid such as an inorganic acid, for example, a hydrohalic such as hydrochloric or hydrobromic, sulfuric, nitric, phosphoric and the like; or an organic acid, such as, for example, acetic, hydroxyacetic, propanoic, lactic, pyruvic, malonic, succinic, maleic, fumaric, malic, tartaric, citric, methanesulfonic, ethanesulfonic, benzenesulfonic, p-toluenesulfonic, cyclamic, salicylic, p-aminosalicylic, pamoic and the like.

The compounds of formula (1) containing acidic protons may be converted into their therapeutically active, non-toxic base addition salt form, e.g. metal or amine salts, by treatment with appropriate organic and inorganic bases. Appropriate base salt forms include, for example, animonium salts, alkali and earth alkaline metal salts, e.g. lithium, sodium, potassium, magnesium, calcium salts and the like, salts with organic bases, e.g. N-methyl-D-glucamine, hydrabamine salts, and salts with amino acids such as, for example, arginine, lysine and the like.

Conversely said salt forms can be converted into the free forms by treatment with an appropriate base or acid.

Compounds of the formula I and their salts can be in the form of a solvate, which is included within the scope of the present invention. Such solvates include for example hydrates, alcoholates and the like.

Many of the compounds of formula I and some of their intermediates have at least one stereogenic center in their structure. This stereogenic center may be present in a R or a S configuration, said R and S notation is used in correspondence with the rules described in Pure Appl. Chem. (1976), 45, 11–30.

The invention also relates to all stereoisomeric forms such as enantiomeric and diastereoisomeric forms of the compounds of formula I or mixtures thereof (including all possible mixtures of stereoisomers).

Furthermore, certain compounds of formula I which contain alkenyl groups may exist as Z (zusammen) or E (entgegen) isomers. In each instance, the invention includes both mixture and separate individual isomers.

Multiple substituents on the piperidinyl or the azepanyl ring can also stand in either cis or trans relationship to each other with respect to the plane of the piperidinyl or the azepanyl ring.

Some of the compounds of formula I may also exist in tautomeric forms. Such forms although not explicitly indicated in the above formula are intended to be included within the scope of the present invention.

With respect to the present invention reference to a compound or compounds is intended to encompass that compound in each of its possible isomeric forms and mixtures thereof unless the particular isomeric form is referred to specifically.

The invention also includes within its scope prodrug forms of the compounds of formula I and its various sub-scopes and sub-groups.

The term "prodrug" as used herein includes compound forms which are rapidly transformed in vivo to the parent compound according to the invention, for example, by hydrolysis in blood. Prodrugs are compounds bearing groups which are modified by biotransformation prior to exhibiting their pharmacological action. Such groups include moieties which are readily oxidised, cyclised or cleaved, which compound after biotransformation remains or becomes pharmacologically active. For example, metabolically cleavable groups form a class of groups well known to practitioners of the art. They include, but are not limited to such groups as alknoyl (i.e. acetyl, propionyl, butyryl, and the like), unsubstituted and substituted carbocyclic aroyl (such as benzoyl, substituted benzoyl and 1- and 2-naphthoyl), alkoxycarbonyl (such as ethoxycarbonyl), trialkylsilyl (such as trimethyl- and triethylsilyl), monoesters formed with dicarboxylic acids (such as succinyl), phosphate, sulfate, sulfonate, sulfonyl, sulfinyl and the like. The compounds bearing the biotransformable groups have the advantage that they may exhibit improved bioavailability as a result of enhanced solubility and/or rate of absorption conferred upon the parent compound by virtue of the presence of the biotransformable group. T. Higuchi and V. Stella, "Pro-drugs as Novel Delivery System", Vol. 14 of the A.C.S. Symposium Series; "Bioreversible Carriers in Drug Design", ed. Edward B. Roche, American Pharmaceutical Association and Pergamon Press, 1987.

The term "R substituent" refers to $R^1$, $R^2$, $R^3$, $R^4$ or $R^5$, independently.

According to a preferred embodiment, the present invention relates to a compound of formula I as defined above wherein n represents 0. The compound is a 6-ring structure (2-thioxo- or 2-oxo-piperidinyl derivative) wherein $R^1$ is not existent since n=0, and is depicted by the formula (I-A).

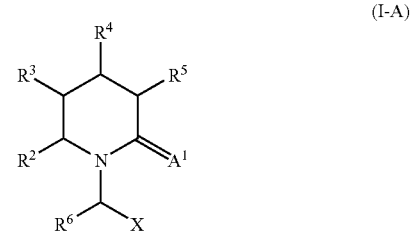

(I-A)

According to a following embodiment, the present invention relates to a compound of formula I according to the invention as defined above wherein n represents 1. The compound is a 7-ring structure (2-thioxo- or 2-oxo-azepanyl derivative) wherein $R^1$ is existent since n=1 and depicted by the formula (I-B).

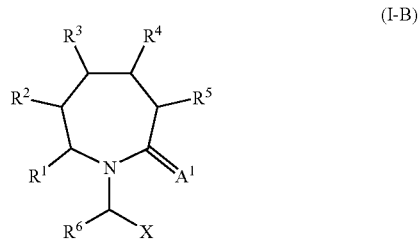

(I-B)

According to a more preferred embodiment, the invention relates to said compound as defined above wherein n=0, $R^3$ and/or $R^4$ are different from hydrogen and $R^2$ and $R^5$ represent hydrogen.

According to another more preferred embodiment, the invention relates to said compound as defined above wherein n–1, $R^2$, $R^3$ and/or $R^4$ are different from hydrogen and wherein $R^1$ and $R^5$ represent hydrogen.

According to a yet more preferred embodiment, the invention relates to said compound as defined above wherein only one R substituent chosen from $R^3$ or $R^4$ when n=0 or from $R^2$, $R^3$ or $R^4$ when n—1, is different from hydrogen and the remaining R substituent(s) is/are hydrogen. We hereby refer to a mono-substituted 2-thioxo- or 2-oxo-piperidinyl or 2-thioxo- or 2-oxo-azepanyl derivatives.

According to another preferred embodiment, the present invention relates to compounds of formula I according to the invention as defined above wherein $A^1$ represents an oxygen atom. We hereby refer to 2-oxo-piperidinyl or 2-oxo-azepanyl derivatives.

According to another preferred embodiment, the present invention relates to compounds of formula I according to the invention as defined above wherein X is $CONR^7R^8$, especially CONH$_2$. We hereby refer to amido derivatives of 2-oxo(or thioxo)-piperidinyl or 2-oxo(or thioxo)-azepanyl.

According to another preferred embodiment, the present invention relates to compounds of formula I according to the invention as defined above wherein R$^6$ represents hydrogen, C1–4 alkyl, or a CH$_2$—R$^{6a}$ group wherein R$^{6a}$ represents a heterocycle. Most preferably R$^6$ is a C1–4 alkyl, especially ethyl. When R$^6$ is ethyl we refer to 2-(2-oxo(or thioxo)-1-piperidinyl)butanamide or 2-(2-oxo(or thioxo)-1-azepanyl) butanamide derivatives.

According to another preferred embodiment, the present invention relates to compounds of formula I according to the invention as defined above wherein the carbon atom to which R$^6$ is attached is of the S configuration. In case where R$^6$ is ethyl, A is oxygen and X is CON R$^7$, R$^8$ we refer then to (2S)-2-(2-oxo-1-piperidinyl)butanamide or (2S)-2-(2-oxo-1-azepanyl)butanamide derivatives.

According to a prefered embodiment, the present invention relates to a compound as defined above wherein R$^2$ when n=1, R$^3$ and R$^4$ are the same or different and each is independently hydrogen, halogen, nitro, nitrooxy, cyano, carboxy, amido, sulfonic acid, sulfonamide, alkyl, alkenyl, alkynyl, ester, ether, aryl, heterocycle, acyl derivative, sulfonyl derivative or sulfinyl derivative;

R$^1$ when existent, R$^2$ when n=0 and R$^5$ are hydrogen;

R$^6$ is hydrogen, alkyl, aryl or —CH$_2$—R$^{6a}$ wherein R$^{6a}$ is aryl, heterocycle, halogen, hydroxy, amino, nitro or cyano;

provided that, when R$^6$ is hydrogen, X is —CONR$^7$R$^8$ and that the compound is neither methyl (2R)-2-[(6R)-6-methyl-2-oxoazepanyl]-3-phenylpropanoate nor methyl (2S)-2-[(4R)-4-methyl-2-oxoazepanyl]-3-phenylpropanoate.

According to this preferred embodiment, the compound is generally such that when R$^6$ is benzyl, X is —COOCH$_3$ and n=1, R$^2$ is different from methyl when R$^3$ and R$^4$ are both hydrogen and R$^4$ is different from methyl when R$^2$ and R$^3$ are both hydrogen.

According to another preferred embodiment, the present invention relates to a compound as defined above wherein R$^2$ when n=1, R$^3$ and R$^4$ are the same or different and each is independently hydrogen; cyano; carboxy; amido;

C1–12 alkyl, each optionally substituted by one or more substituents selected from hydroxy, halogen, cyano, thiocyanato, alkoxy, azido, alkyltio, cycloalkyl, acyl, aryl and heterocycle;

C2–12 alkenyl, each optionally substituted by one or more substituents selected from halogen, cyano, thiocyanato, azido, alkylthio, alkyl, aryl and acyl;

C2–12 alkynyl, each optionally substituted by one or more substituents selected from halogen, cyano, thiocyanato, azido, alkylthio, alkyl, aryl and acyl;

acyl derivative of formula —CO—R$^{11}$, wherein R$^{11}$ is selected from C1–12 alkyl, C2–12 alkenyl, C2–12 alkynyl, heterocycle and aryl;

ester of formula —CO—O—R$^{11}$ wherein R$^{11}$ is selected from C1–12 alkyl, C2–12 alkenyl, C2–12 alkynyl and aryl;

heterocycle selected from triazolyl, tetrazolyl, pyrrolidinyl, pyridyl, 1-oxidopyridyl, thiomorpholinyl, benzodioxolyl, furyl, oxazolyl, pyrimidinyl, pyrrolyl, thiadiazolyl, thiazolyl, thienyl and piperazinyl, each optionally substituted by one or more substituents selected from halogen, alkyl, substituted alkyl, alkoxy, nitro, amino, acyl and phenyl;

aryl, each optionally substituted by one or more substituents selected from C1–6 alkyl, C1–6 haloalkyl, C1–6 alkoxy, C1–6 alkylthio, amino, azido, sulfonyl, aryl and nitro.

According to another preferred embodiment, the present invention relates to a compound as defined above, wherein R$^2$ when n=1, R$^3$ and R$^4$ are the same or different and each is independently hydrogen;

C1–7 alkyl, each optionally substituted by one or more substituents selected from hydroxy, halogen, cyano, thiocyanato, alkoxy, azido, alkyltio, cyclopropyl, acyl and phenyl;

C2–6 alkenyl, each optionally substituted by one or more substituents selected from halogen, cyano, thiocyanato, azido, alkylthio, cycloalkyl, phenyl and acyl;

C2–6 alkynyl, each optionally substituted by one or more substituents selected from halogen, cyano, thiocyanato, azido, alkylthio, cycloalkyl, phenyl and acyl;

heterocycle selected from tetrazolyl, pyrrolidinyl, pyridyl, furyl, pyrrolyl, thiazolyl and thienyl, each optionally substituted by one or more substituents selected from halogen, alkyl, halogen substituted alkyl, acyl, alkoxy, nitro, amino and phenyl;

phenyl, each optionally substitued by one or more substituents selected from C1–6 alkyl, halogen substituted alkyl, halogen, alkoxy, amino, azido, sulfonyl, phenyl and nitro.

According to another preferred embodiment, the present invention relates to a compound as defined above wherein at least one of the R substituents chosen from the group R$^2$, R$^3$ and R$^4$ when n=1 or from the group R$^3$ and R$^4$ when n=0, represents independently C1–4-alkyl or C3–7-cycloalkyl, optionally substituted by one or more halogen, hydroxy, lower alkyl and/or azido.

According to another preferred embodiment, the present invention relates to a compound as defined above wherein at least one of the R substituents chosen from the group R$^2$, R$^3$ and R$^4$ when n=1 or from the group R$^3$ and R$^4$ when n=0, represents independently vinyl, optionally substituted by one or more halogen or/and lower alkyl.

According to another preferred embodiment, the present invention relates to a compound as defined above wherein at least one of the R substituents chosen from the group R$^2$, R$^3$ and R$^4$ when n=1 or from the group R$^3$ and R$^4$ when n=0, represents independently ethynyl, propynyl or butynyl, optionally substituted by one or more halogen and/or lower alkyl.

According to another preferred embodiment, the present invention relates to a compound as defined above wherein at least one of the R substituents chosen from the group R$^2$, R$^3$ and R$^4$ when n=1 or from the group R$^3$ and R$^4$ when n=0, represents independently phenyl, optionally substituted by one or more halogen, lower alkyl, azido and/or nitro.

According to another preferred embodiment, the present invention relates to a compound as defined above wherein at least one of the R substituents chosen from the group R$^2$, R$^3$ and R$^4$ when n=1 or from the group R$^3$ and R$^4$ when n=0, represents independently 2- or 3-thienyl, optionally substituted by one or more halogen, acyl, cyano or/and lower alkyl.

According to a particular preferred embodiment, the present invention relates to a compound as defined above wherein at least one of the R substituents chosen from the group R$^3$, R$^4$ and R$^2$ when n=1 or from the group R$^3$ and R$^4$ when n=0, is hydroxymethyl, propyl, butyl, 3,3,3-trifluoropropyl, 2,2,2-trifluoroethyl, cyclopropylmethyl, iodomethyl, azidomethyl, 2-thienyl, 3-thienyl, phenyl, 3-chlorophenyl, 3-azidophenyl, 2,2-difluorovinyl, 2,2-dibromovinyl, 2,2-dichlorovinyl, 2-ethynyl, 5-methyl-2-thienyl, 5-formyl-2-ethynyl, 5-cyano-2-thienyl, 3-bromo-2-thienyl, 4-methyl-2-thienyl, 3,3,3-trifluoro-1-propynyl, 1-propynyl, cyclopropylethynyl, 3-methyl-1-butynyl, 1-butynyl, 2,2-difluoropropyl, 2-chloro-2,2-difluoroethyl, 2-bromo-2,2-difluoroethyl and 2-iodo-2,2-difluoroethyl.

According to yet another preferred embodiment, the present invention relates to a compound as defined above wherein $R^1$, $R^2$, $R^4$ and $R^5$ are hydrogen.

According to even another preferred embodiment, the present invention relates to a compound as defined above wherein $R^1$, $R^2$, $R^3$ and $R^5$ are hydrogen.

According to even another preferred embodiment, the present invention relates to a compound as defined above wherein n=1 and $R^1$, $R^3$, $R^4$ and $R^5$ are hydrogen.

In all the above-mentioned scopes when the carbon atom to which $R^6$ is attached is asymmetric it is preferably in the "S"-configuration.

Representative compounds of this invention as defined above are selected from the group consisting of 2-[5-(hydroxymethyl)-2-oxo-1-piperidinyl]butanamide, 2-(2-oxo-5-propyl-1-piperidinyl)butanamide, 2-[2-oxo-5-(3,3,3-trifluoropropyl)-1-piperidinyl]butanamide, 2-[5-(cyclopropylmethyl)-2-oxo-1-piperidinyl]butanamide, 2-[5-(iodomethyl)-2-oxo-1-piperidinyl]butanamide, 2-[5-(azidomethyl)-2-oxo-1-piperidinyl]butanamide, 2-(2-oxo-5-phenyl-1-piperidinyl)butanamide, 2-[2-oxo-5-(2-thienyl)-1-piperidinyl]butanamide, 2-[2-oxo-5-(3-thienyl)-1-piperidinyl]butanamide, 2-[5-(3-chlorophenyl)-2-oxo-1-piperidinyl]butanamide, 2-[5-(3-azidophenyl)-2-oxo-1-piperidinyl]butanamide, 2-[5-(2,2-difluorovinyl)-2-oxo 1-piperidinyl]butanamide, 2-[5-(2,2-dibromovinyl)-2-oxo-1-piperidinyl]butanamide, 2-[5-(2,2-dichlorovinyl)-2-oxo-1-piperidinyl]butanamide, 2-(5-ethynyl-2-oxo-1-piperidinyl)butanamide, 2-[5-(5-methyl-2-thienyl)-2-oxo-1-piperidinyl]butanamide, 2-[5-(5-formyl-2-thienyl)-2-oxo-1-piperidinyl]butanamide, 2-[5-(5-cyano-2-thienyl)-2-oxo-1-piperidinyl]butanamide, 2-[5-(3-bromo-2-thienyl)-2-oxo-1-piperidinyl]butanamide, 2-[5-(4-methyl-2-thienyl)-2-oxo-1-piperidinyl]butanamide, 2-[2-oxo-5-(3,3,3-trifluoro-1-propynyl)-1-piperidinyl]butanamide, 2-[2-oxo-5-(1-propynyl)-1-piperidinyl]butanamide, 2-[5-(cyclopropylethynyl)-2-oxo-1-piperidinyl]butanamide, 2-[5-(3-methyl-1-butynyl)-2-oxo-1-piperidinyl]butanamide, 2-[5-(1-butynyl)-2-oxo-1-piperidinyl]butanamide, 2-[5-(2,2-difluoropropyl)-2-oxo 1-piperidinyl]butanamide, 2-[5-(2-chloro-2,2-difluoroethyl)-2-oxo-1-piperidinyl]butanamide, 2-[5-(2-bromo-2,2-difluoroethyl)-2-oxo-1-piperidinyl]butanamide, 2-[4-(hydroxymethyl)-2-oxo-1-piperidinyl]butanamide, 2-(2-oxo-4-propyl-1-piperidinyl)butanamide, 2-[2-oxo-4-(3,3,3-trifluoropropyl)-1-piperidinyl]butanamide, 2-[4-(cyclopropylmethyl)-2-oxo-1-piperidinyl]butanamide, 2-[4-(iodomethyl)-2-oxo-1-piperidinyl]butanamide, 2-[4-(azidomethyl)-2-oxo-1-piperidinyl]butanamide, 2-(2-oxo-4-phenyl-1-piperidinyl)butanamide, 2-[2-oxo-4-(2-thienyl)-1-piperidinyl]butanamide, 2-[2-oxo-4-(3-thienyl)-1-piperidinyl]butanamide, 2-[4-(3-chlorophenyl)-2-oxo-1-piperidinyl]butanamide, 2-[4-(3-azidophenyl)-2-oxo-1-piperidinyl]butanamide, 2-[4-(2,2-difluorovinyl)-2-oxo-1-piperidinyl]butanamide, 2-[4-(2,2-dibromovinyl)-2-oxo-1-piperidinyl]butanamide, 2-[4-(2,2-dichlorovinyl)-2-oxo-1-piperidinyl]butanamide, 2-(4-ethynyl-2-oxo-1-piperidinyl)butanamide, 2-[4-(5-methyl-2-thienyl)-2-oxo-1-piperidinyl]butanamide, 2-[4-(5-formyl-2-thienyl)-2-oxo-1-piperidinyl]butanamide, 2-[4-(5-cyano-2-thienyl)-2-oxo-1-piperidinyl]butanamide, 2-[4-(3-bromo-2-thienyl)-2-oxo-1-piperidinyl]butanamide, 2-[4-(4-methyl-2-thienyl)-2-oxo-1-piperidinyl]butanamide, 2-[2-oxo-4-(3,3,3-trifluoro-1-propynyl)-1-piperidinyl]butanamide, 2-[2-oxo-4-(1-propynyl)-1-piperidinyl]butanamide, 2-[4-(cyclopropylethynyl)-2-oxo-1-piperidinyl]butanamide, 2-[4-(3-methyl-1-butynyl)-2-oxo-1-piperidinyl]butanamide, 2-[4-(1'-butynyl)-2-oxo-1-piperidinyl]butanamide, 2-[4-(2,2-difluoropropyl)-2-oxo-1-piperidinyl]butanamide, 2-[4-(2-chloro-2,2-difluoroethyl)-2-oxo-1-piperidinyl]butanamide, 2-[4-(2-bromo-2,2-difluoroethyl)-2-oxo-1-piperidinyl]butanamide, 2[4-(2,2,2-trifluoroethyl)-2-oxo-1-piperidinyl]butanamide, 2-[5-(hydroxymethyl)-2-oxo-1-azepanyl]butanamide, 2-(2-oxo-5-propyl-1-azepanyl)butanamide, 2-[2-oxo-5-(3,3,3-trifluoropropyl)-1-azepanyl]butanamide, 2-[5-(cyclopropylmethyl)-2-oxo-1-azepanyl]butanamide, 2-[5-(iodomethyl)-2-oxo-1-azepanyl]butanamide, 2-[5-(azidomethyl)-2-oxo-1-azepanyl]butanamide, 2-(2-oxo-5-phenyl-1-azepanyl)butanamide, 2-[2-oxo-5-(2-thienyl)-1-azepanyl]butanamide, 2-[2-oxo-5-(3-thienyl)-1-azepanyl]butanamide, 2-[5-(3-chlorophenyl)-2-oxo-1-azepanyl]butanamide, 2-[5-(3-azidophenyl)-2-oxo-1-azepanyl]butanamide, 2-[5-(2,2-difluorovinyl)-2-oxo-1-azepanyl]butanamide, 2-[5-(2,2-dibromovinyl)-2-oxo-1-azepanyl]butanamide, 2-[5-(2,2-dichlorovinyl)-2-oxo-1-azepanyl]butanamide, 2-(5-ethynyl-2-oxo-1-azepanyl)butanamide, 2-[5-(5-methyl-2-thienyl)-2-oxo-1-azepanyl]butanamide, 2-[5-(5-formyl-2-thienyl)-2-oxo-1-azepanyl]butanamide, 2-[5-(5-cyano-2-thienyl)-2-oxo-1-azepanyl]butanamide, 2-[5-(3-bromo-2-thienyl)-2-oxo-1-azepanyl]butanamide, 2-[5-(4-methyl-2-thienyl)-2-oxo 1-azepanyl]butanamide, 2-[2-oxo-5-(3,3,3-trifluoro-1-propynyl)-1-azepanyl]butanamide, 2-[2-oxo-5-(1-propynyl)-1-azepanyl]butanamide, 2-[5-(cyclopropylethynyl)-2-oxo-1-azepanyl]butanamide, 2-[5-(3-methyl-1-butynyl)-2-oxo-1-azepanyl]butanamide, 2-[5-(1-butynyl)-2-oxo-1-azepanyl]butanamide, 2-[5-(2,2-difluoropropyl)-2-oxo-1-azepanyl]butanamide, 2-[5-(2-chloro-2,2-difluoroethyl)-2-oxo-1-azepanyl]butanamide, 2-[5-(2-bromo-2,2-difluoroethyl)-2-oxo-1-azepanyl]butanamide, 2-[5-(2,2,2-trifluoroethyl)-2-oxo-1-azepanyl]butanamide, 2-[6-(hydroxymethyl)-2-oxo-1-azepanyl]butanamide, 2-(2-oxo-6-propyl-1-azepanyl)butanamide, 2-[2-oxo-6-(3,3,3-trifluoropropyl)-1-azepanyl]butanamide, 2-[6-(cyclopropylmethyl)-2-oxo-1-azepanyl]butanamide, 2-[6-(iodomethyl)-2-oxo-1-azepanyl]butanamide, 2-[6-(azidomethyl)-2-oxo-1-azepanyl]butanamide, 2-(2-oxo-6-phenyl-1-azepanyl)butanamide, 2-[2-oxo-6-(2-thienyl)-1-azepanyl]butanamide, 2-[2-oxo-6-(3-thienyl)-1-azepanyl]butanamide, 2-[6-(3-chlorophenyl)-2-oxo-1-azepanyl]butanamide, 2-[6-(3-azidophenyl)-2-oxo-1-azepanyl]butanamide, 2-[6-(2,2-difluorovinyl)-2-oxo-1-azepanyl]butanamide, 2-[6-(2,2-dibromovinyl)-2-oxo-1-azepanyl]butanamide, 2-[6-(2,2-dichlorovinyl)-2-oxo-1-azepanyl]butanamide, 2-(6-ethynyl-2-oxo-1-azepanyl)butanamide, 2-[6-(5-methyl-2-thienyl)-2-oxo-1-azepanyl]butanamide, 2-[6-(5-formyl-2-thienyl)-2-oxo-1-azepanyl]butanamide, 2-[6-(5-cyano-2-thienyl)-2-oxo-1-azepanyl]butanamide, 2-[6-(3-bromo-2-thienyl)-2-oxo-1-azepanyl]butanamide, 2-[6-(4-methyl-2-thienyl)-2-oxo-1-azepanyl]butanamide, 2-[2-oxo-6-(3,3,3-trifluoro-1-propynyl)-1-azepanyl]butanamide, 2-[2-oxo-6-(1-propynyl)-1-azepanyl]butanamide, 2-[6-(cyclopropylethynyl)-2-oxo-1-azepanyl]butanamide, 2-[6-(3-methyl-1-butynyl)-2-oxo-1-azepanyl]butanamide, 2-[6-(1-butynyl)-2-oxo-1-azepanyl]butanamide, 2-[6-(2,2-difluoropropyl)-2-oxo-1-azepanyl]butanamide, 2-[6-(2-chloro-2,2-difluoroethyl)-2-oxo-1-azepanyl]butanamide, 2-[6-(2-bromo-2,2-difluoroethyl)-2-oxo-1-azepanyl]butanamide, 2-[6-(2,2,2-trifluoroethyl)-2-oxo-1-azepanyl]butanamide, 2-[4-(hydroxymethyl)-2-oxo-1-azepanyl]butanamide, 2-(2-oxo-4-propyl-1-azepanyl)butanamide, 2-[2-oxo-4-(3,3,3-trifluoropropyl)-1-azepanyl]butanamide, 2-[4-(cyclopropylmethyl)-2-oxo-1-azepanyl]butanamide, 2-[4-(iodomethyl)-2-oxo-1-azepanyl]

butanamide, 2-[4-(azidomethyl)-2-oxo-1-azepanyl]butanamide, 2-(2-oxo-4-phenyl-1-azepanyl)butanamide, 2-[2-oxo-4-(2-thienyl)-1-azepanyl]butanamide, 2-[2-oxo-4-(3-thienyl)-1-azepanyl]butanamide, 2-[4-(3-chlorophenyl)-2-oxo-1-azepanyl]butanamide, 2-[4-(3-azidophenyl)-2-oxo-1-azepanyl]butanamide, 2-[4-(2,2-difluorovinyl)-2-oxo-1-azepanyl]butanamide, 2-[4-(2,2-dibromovinyl)-2-oxo-1-azepanyl]butanamide, 2-[4-(2,2-dichlorovinyl)-2-oxo-1-azepanyl]butanamide, 2-(4-ethynyl-2-oxo-1-azepanyl) butanamide, 2-[4-(5-methyl-2-thienyl)-2-oxo-1-azepanyl] butanamide, 2-[4-(5-formyl-2-thienyl)-2-oxo-1-azepanyl] butanamide, 2-[4-(5-cyano-2-thienyl)-2-oxo-1-azepanyl] butanamide, 2-[4-(3-bromo-2-thienyl)-2-oxo-1-azepanyl] butanamide, 2-[4-(4-methyl-2-thienyl)-2-oxo-1-azepanyl] butanamide, 2-[2-oxo-4-(3,3,3-trifluoro-1-propynyl)-1-azepanyl]butanamide, 2-[2-oxo-4-(1-propynyl)-1-azepanyl] butanamide, 2-[4-(cyclopropylethynyl)-2-oxo-1-azepanyl] butanamide, 2-[4-(3-methyl-1-butynyl)-2-oxo-1-azepanyl] butanamide, 2-[4-(1-butynyl)-2-oxo-1-azepanyl] butanamide, 2-[4-(2,2-difluoropropyl)-2-oxo-1-azepanyl] butanamide, 2-[4-(2-chloro-2,2-difluoroethyl)-2-oxo-1-azepanyl]butanamide, 2-[4-(2-bromo-2,2-difluoroethyl)-2-oxo 1-azepanyl]butanamide, 2-[4-(2,2,2-trifluoroethyl)-2-oxo-1-azepanyl]butanamide.

The best results have been obtained with the following compounds:

(2S)-2-[5-(iodomethyl)-2-oxo-1-piperidinyl]butanamide,
(2S)-2-[5-(azidomethyl)-2-oxo-1-piperidinyl]butanamide,
2-(2-oxo-5-phenyl-1-piperidinyl]butanamide,
(2S)-2-[4-(iodomethyl)-2-oxo-1-piperidinyl]butanamide,
2-[5-(iodomethyl)-2-oxo-1-azepanyl]butanamide.

It has now been found that compounds of formula I and their pharmaceutically acceptable salts are useful in a variety of pharmaceutical indications.

For example, the compounds according to the invention are useful for the treatment of epilepsy, epileptogenesis, seizure disorders and convulsions.

These compounds may also be used for the treatment of other neurological disorders including bipolar disorders, mania, depression, anxiety, migraine, trigeminal and other neuralgia, chronic pain, neuropathic pain, cerebral ischemia, cardiac arrhythmia, myotonia, cocaine abuse, stroke, myoclonus, essential tremor, dyskinesia and other movement disorders, neonatal cerebral haemorrhage, amyotrophic lateral sclerosis, spasticity, Parkinson's disease and other neurodegenerative diseases.

In addition the compounds according to the invention may be used in the treatment of bronchial asthma, asthmatic status and allergic bronchitis, asthmatic syndrome, bronchial hyperreactivity and bronchospastic syndromes as well as allergic and vasomotor rhinitis and rhinoconjunctivitis.

Thus, the present invention, in a further aspect, concerns the use of a compound of formula I or a pharmaceutically acceptable salt thereof for the manufacture of a medicament for the treatment of neurological and other disorders such as mentioned above.

In particular, the present invention concerns the use of a compound of formula I or a pharmaceutically acceptable salt thereof, for the manufacture of a medicament for the treatment of epilepsy, bipolar disorders, chronic pain or neuropathic pain, migraine, bronchial-, asthmatic- or allergic conditions.

In particular, the present invention concerns the use of a compound as defilmed above for the manufacture of a medicin for the treatment of epilepsy, epileptogenesis, seisure disorders and convulsions.

The activity and properties of the active compounds, oral availability and stability in vitro or in vivo can vary significantly among the optical isomers of the disclosed compounds.

In a preferred embodiment, the active compound is administered in an enantiomerically enriched form, i.e., substantially in the form of one isomer.

The present invention also concerns a method for treating epilepsy, epileptogenesis, seizure disorders, convulsions and other neurological disorders including bipolar disorders, mania, depression, anxiety, migraine, trigeminal and other neuralgia, chronic pain, neuropathic pain, cerebral ischemia, cardiac arrhythmia, myotonia, cocaine abuse, stroke, myoclonus, essential tremor, dyskinesia and other movement disorders, neonatal cerebral haemorrhage, amyotrophic lateral sclerosis, spasticity, Parkinson's disease and other degenerative diseases, bronchial asthma, asthmatic status and allergic bronchitis, asthmatic syndrome, bronchial hyperreactivity and bronchospastic syndromes as well as allergic and vasomotor rhinitis and rhinoconjunctivitis, in a mammal in need of such treatment, comprising administering a therapeutic dose of at least one compound as defined above.

The present invention also concerns a method for treating epilepsy, migraine, bipolar disorders, chronic pain or neuropathic pain or bronchial-, asthmatic- or allergic conditions, in a mammal in need of such treatment, comprising administering a therapeutic dose of at least one compound of formula I or a pharmaceutically acceptable salt thereof to a patient.

The present invention also concerns a method for treating epilepsy, epileptogenesis, seizure disorders and convulsions.

The methods of the invention comprise administration to a mammal (preferably human) suffering from above mentioned conditions or disorders, of a compound according to the invention in an amount sufficient to alleviate or prevent the disorder or condition.

The compound is conveniently administered in any suitable unit dosage form, including but not limited to one containing 5 to 1000 mg, preferably 25 to 500 mg of active ingredient per unit dosage form.

The term "treatment" as used herein includes curative treatment and prophylactic treatment.

By "curative" is meant efficacy in treating a current symptomatic episode of a disorder or condition.

By "prophylactic" is meant prevention of the occurrence or recurrence of a disorder or condition.

The term "epilepsy" as used herein refers to a disorder of brain function characterised by the periodic and unpredictable occurrence of seizures. Seizures can be "non-epileptic" when evoked in a normal brain by treatments such as electroshock or chemical convulsants or "epileptic" when evoked without evident provocation.

The term "seizure" as used herein refers to a transient alteration of behaviour due to the disordered, synchronous, and rhythmic firing of populations of brain neurones.

The term "migraine" as used herein means a disorder characterised by recurrent attacks of headache that vary widely in intensity, frequency, and duration. The attacks are commonly unilateral and are usually associated with anorexia, nausea, vomiting, phonophobia, and/or photophobia. In some cases they are preceded by, or associated with, neurological and mood disturbances. Migraine headache may last from 4 hours to about 72 hours. The International Headache Society ([HS, 1988) classifies migraine with aura (classical migraine) and migraine without aura (common migraine) as the major types of migraine. Migraine with aura consists of a headache phase preceded by characteristic visual, sensory, speech, or motor symptoms. In the absence of such symptoms, the headache is called migraine without aura.

The term "bipolar disorders" as used herein refers to those disorders classified as Mood Disorders according to the Diagnostic and Statistical Manual of Mental Disorders, 4th edition (Diagnostic and Statistical Manual of Mental Disorders (DSM-IV TM), American Psychiatry Association, Washington, D.C., 1994). Bipolar disorders are generally characterised by spontaneously triggered repeated (i.e. at least two) episodes in which the patient's hyperexcitability, activity and mood are significantly disturbed, this disturbance consisting on some occasions of an elevation of mood and increased energy and activity (mania or hypomania), and in other occasions a lowering of mood and decreased energy and activity (depression). Bipolar disorders are separated into four main categories in the DSM-IV (bipolar I disorder, bipolar II disorder, cyclothymia, and bipolar disorders not otherwise specified).

The term "manic episode", as used herein refers to a distinct period during which there is an abnormally and persistently elevated, expansive, or irritable mood with signs of pressured speech and psychomotor agitation.

The term "hypomania", as used herein refers to a less extreme manic episode, with lower grade of severity.

The term "major depressive episode", as used herein refers to a period of at least 2 weeks during which there is either depressed mood or the loss of interest or pleasure in nearly all activities with signs of impaired concentration and psychomotor retardation.

The term "mixed episode", as used herein refers to a period of time (lasting at least 1 week) in which the criteria are met both for a manic episode and for a major depressive episode nearly every day.

The term "chronic pain" as used herein refers to the condition gradually being recognised as a disease process distinct from acute pain. Conventionally defined as pain that persists beyond the normal time of healing, pain can also be considered chronic at the point when the individual realises that the pain is going to be a persistent part of their lives for the foreseeable future. It is likely that a majority of chronic pain syndromes involves a neuropathic component, which is usually harder to treat than acute somatic pain.

The term "neuropathic pain" as used herein refers to pain initiated by a pathological change in a nerve which signals the presence of a noxious stimulus when no such recognisable stimulus exists, giving rise to a false sensation of pain. In other words, it appears that the pain system has been turned on and cannot turn itself off.

The activity of the compounds of formula I, or their pharmaceutically acceptable salts, as anticonvulsants can be determined in the audiogenic seizures model. The objective of this test is to evaluate the anticonvulsant potential of a compound by means of audiogenic seizures induced in sound-susceptible mice, a genetic animal model with reflex seizures. In this model of primary generalised epilepsy, seizures are evoked without electrical or chemical stimulation and the seizure types are, at least in part, similar in their clinical phenomenology to seizures occurring in man (Löscher W. & Schmidt D., Epilepsy Res. (1998), 2, 145–181; Buchhalter J. R., Epilepsia (1993), 34, S31–S41). Results obtained with compounds of formula I are indicative of a strong pharmacological effect (Table III A, III B).

Another assay indicative of potential anticonvulsant activity is binding to levetiracetam binding site (LBS) as hereinafter described (Table III A, III B).

The activity of the compounds of formula I, or their pharmaceutically acceptable salts, in chronic neuropathic pain can be determined in animal models. For example, chronic neuropathic pain can be modelled by pharmacologically inducing diabetes in rats. In this model, animals show progressive hyperalgesia to nociceptive stimuli, a symptom generally observed in patients with painful peripheral neuropathy (Courteix C, Eschalier, A. and Lavarenne J., Pain (1993), 53, 81–88). This model was shown to possess a high pharmacological predictivity (Courteix C, Bardin M., Chantelauze C., Lavarenne J and Eschalier, A., Pain, 57 (1994) 153–160).

The activity of the compounds of formula I, or their pharmaceutically acceptable salts, in bipolar disorders can be assessed in animal models. For example, bipolar disorders and especially mania can be modelled by pharmacologically inducing hyperactivity in rats and evaluating their behaviour in an Y maze. In such a situation, therapeutic agents effective in man, like Lithium and sodium valproate decrease the hyperactivity, thus validating the predictivity of the model (Cao B. J. and Peng N. A., Eur. J. Pharmacol. (1993), 237, 177–181; Vale A. L. and Ratcliffe F. Psychopharmacology, 91 (1987) 352–355).

Potential anti-asthmatic properties of the compounds of formula I, or their pharmaceutically acceptable salts would be tested for in an animal model of allergic asthma, in which guinea pigs sensitised to ovalbumin are challenged with the antigen and investigated for changes in pulmonary function and airway inflammatory cell content. (Yamada et al. (1992) Development of an animal model of late asthmatic response in guinea pigs and effects anti-asthmatic drugs. Prostaglandins, 43: 507–521).

Activity in any of the above mentioned indications can of course be determined by carrying out suitable clinical trials in a manner known to a person skilled in the relevant art for the particular indication and/or in the design of clinical trials in general.

For treating diseases, compounds of formula I or their pharmaceutically acceptable salts may be employed at an effective daily dosage and administered in the form of a pharmaceutical composition.

Therefore, another embodiment of the present invention concerns a pharmaceutical composition comprising an effective amount of a compound of formula I or a pharmaceutically acceptable salt thereof in combination with a pharmaceutically acceptable diluent or carrier.

To prepare a pharmaceutical composition according to the invention, one or more of the compounds of formula I or a pharmaceutically acceptable salt thereof, is intimately admixed with a pharmaceutical diluent or carrier according to conventional pharmaceutical compounding techniques known to the skilled practitioner.

Suitable diluents and carriers may take a wide variety of forms depending on the desired route of administration, e.g., oral, rectal, or parenteral.

Pharmaceutical compositions comprising compounds according to the invention can, for example, be administered orally or parenterally, i.e., intravenously, intramuscularly or subcutaneously, intrathecally.

Pharmaceutical compositions suitable for oral administration can be solids or liquids and can, for example, be in the form of tablets, pifls, dragees, gelatine capsules, solutions, syrups, and the like.

To this end the active ingredient may be mixed with an inert diluent or a non-toxic pharmaceutically acceptable carrier such as starch or lactose. Optionally, these pharmaceutical compositions can also contain a binder such as microcrystalline cellulose, gum tragacanth or gelatine, a disintegrant such as alginic acid, a lubricant such as magnesium stearate, a glidant such as colloidal silicon dioxide, a sweetener such as sucrose or saccharin, or colouring agents or a flavouring agent such as peppermint or methyl salicylate.

The invention also contemplates compositions which can release the active substance in a controlled manner. Pharmaceutical compositions which can be used for parenteral administration are in conventional form such as aqueous or oily solutions or suspensions generally contained in ampoules, disposable syringes, glass or plastics vials or infusion containers.

In addition to the active ingredient, these solutions or suspensions can optionally also contain a sterile diluent such as water for injection, a physiological saline solution, oils, polyethylene glycols, glycerine, propylene glycol or other synthetic solvents, antibacterial agents such as benzyl alcohol, antioxidants such as ascorbic acid or sodium bisulphite, chelating agents such as ethylene diamine-tetra-acetic acid, buffers such as acetates, citrates or phosphates and agents for adjusting the osmolarity, such as sodium chloride or dextrose.

These pharmaceutical forms are prepared using methods which are routinely used by pharmacists.

The amount of active ingredient in the pharmaceutical compositions can fall within a wide range of concentrations and depends on a variety of factors such as the patient's sex, age, weight and medical condition, as well as on the method of administration. Thus the quantity of compound of formula I in compositions for oral administration is at least 0.5% by weight and can be up to 80% by weight with respect to the total weight of the composition.

In accordance with the invention it has also been found that the compounds of formula I or the pharmaceutically acceptable salts thereof can be administered alone or in combination with other pharmaceutically active ingredients. Non-limiting examples of such additional compounds which can be cited for use in combination with the compounds according to the invention are antivirals, antispastics (e.g. baclofen), antiemetics, antimanic mood stabilizing agents, analgesics (e.g. aspirin, ibuprofen, paracetamol), narcotic analgesics, topical anaesthetics, opioid analgesics, lithium salts, antidepressants (e.g. mianserin, fluoxetine, trazodone), tricyclic antidepressants (e.g. imipramine, desipramine), anticonvulsants (e.g. valproic acid, carbamazepine, phenyloin), antipsychotics (e.g. risperidone, haloperidol), neuroleptics, benzodiazepines (e.g. diazepam, clonazepam), phenothiazines (e.g. chlorpromazine), calcium channel blockers, amphetamine, clonidine, lidocaine, mexiletine, capsaicin, caffeine, quetiapine, serotonin antagonists, β-blockers, antiarrhythmics, triptans, ergot derivatives.

Of particular interest in accordance with the present invention are combinations of at least one compound of formula I or a pharmaceutically acceptable salt thereof and at least one compound inducing neural inhibition mediated by $GABA_A$ receptors. The compounds of formula I exhibit a potentiating effect on the compounds inducing neural inhibition mediated by $GABA_A$ receptors enabling, in many cases, effective treatment of conditions and disorders under reduced risk of adverse effects.

Examples of compounds inducing neural inhibition mediated by $GABA_A$ receptors include the following: benzodiazepines, barbiturates, steroids, and anticonvulsants such as valproate, vigabatrin, tiagabine or pharmaceutical acceptable salts thereof.

Benzodiazepines include the 1,4 benzodiazepines, such as diazepam and clonazepam, and the 1,5-benzodiazepines, such as clobazam. Preferred compound is clonazepam.

Barbiturates include phenobarbital and pentobarbital. Preferred compound is phenobarbital.

Steroids include adrenocorticotropic hormones such as tetracosactide acetate, etc.

Anticonvulsants include hydantoins (phenyloin, ethotoin, etc), oxazolidines (trimethadione, etc.), succinimides (ethosuximide, etc.), phenacemides (phenacemide, acetylphenaturide, etc.), sulfonamides (sulthiame, acetazolamide, etc.), aminobutyric acids (e.g. gamma-amino-beta-hydroxybutyric acid, etc.), sodium valproate and derivatives, carbamazepine and so on.

Preferred compounds include valproic acid, valpromide, valproate pivoxl, sodium valproate, semi-sodium valproate, divalproex, clonazepam, phenobarbital, vigabatrin and tiagabine.

For the preferred oral compositions, the daily dosage is in the range 5 to 1000 milligrams (mg) of compounds of formula I.

In compositions for parenteral administration, the quantity of compound of formula I present is at least 0.5% by weight and can be up to 33% by weight with respect to the total weight of the composition. For the preferred parenteral compositions, the dosage unit is in the range 5 to 1000 mg of compounds of formula I.

The daily dose can fall within a wide range of dosage units of compound of formula I and is generally in the range 5 to 1000 mg. However, it should be understood that the specific doses can be adapted to particular cases depending on the individual requirements, at the physician's discretion.

The amount of the active ingredients (compound I and compound inducing neural inhibition mediated by the $GABA_A$ receptors) in the pharmaceutical composition of the invention will vary depending on the mammal to which the compositions are administered, the disease to be treated, other active ingredients present, etc. Generally, the amount of the compound inducing neural inhibition mediated by the $GABA_A$ receptors and the amount of compound I for a given composition and dosage form can be readily determined employing routine procedures.

According to another aspect, the invention relates to several processes for preparing a compound having the general formula (1) as described above.

The following process description sets forth certain synthesis routes in an illustrative manner. Other alternative and/or analogous methods will be readily apparent to those skilled in this art. As used herein in connection with substituent meanings, "=" means "is" and "≠" means "is other than".

According to one embodiment, compounds having the general formula (I), wherein $A^1$=O and X=—$CONR^7R^8$ or —$COOR^9$, may be made by the cyclisation of an aminoester of formula (A) wherein $Q^1$ represents a linear or branched C1–4-alkyl. Said aminoester of formula (A) wherein n=0 and $R^3$=$COOR^{13}$ or wherein n=1 and $R^2$=$COOR^{13}$, wherein $R^{13}$ represents a linear or branched alkyl group optionally optically active, are obtained by reaction of a compound of formula (B) with an unsaturated diester derivative of formula (C) or (D), respectively, according to the following scheme 1.

the man skilled in the art and is generally carried out between room temperature and 150° C., in the presence or not of a catalyst such as acetic acid, hydroxybenzotriazole or 2-hydroxypyridine. When $Q^1$ does not represent a methyl or ethyl, an ester of formula (A) is hydrolysed under acidic or basic conditions and then cyclised under conventional peptide synthesis conditions, by using coupling agents, for example dicyclohexylcarbodiimide (Bodanszky, M., Bodanszky, A., in "The Practice of Peptide Synthesis", Springer Verlag, 1984).

According to another embodiment, compounds of the general formula (I), wherein $A^1$=O and X=—$CONR^7R^8$ and n=0 may conveniently be made by reaction of a compound of formula (E), wherein $X^1$ represents a halogen atom, preferably an iodine or a chlorine atom, and $X^2$ represents —$OQ^1$ or a halogen atom, preferably a chlorine atom, with a compound of formula (F). Said compound of formula (E) may be obtained by opening of a lactone of formula (G) in the presence of a halogenating agent, for instance TMSI or $SOCl_2$/$ZnCl_2$, followed if necessary by halogenation of the

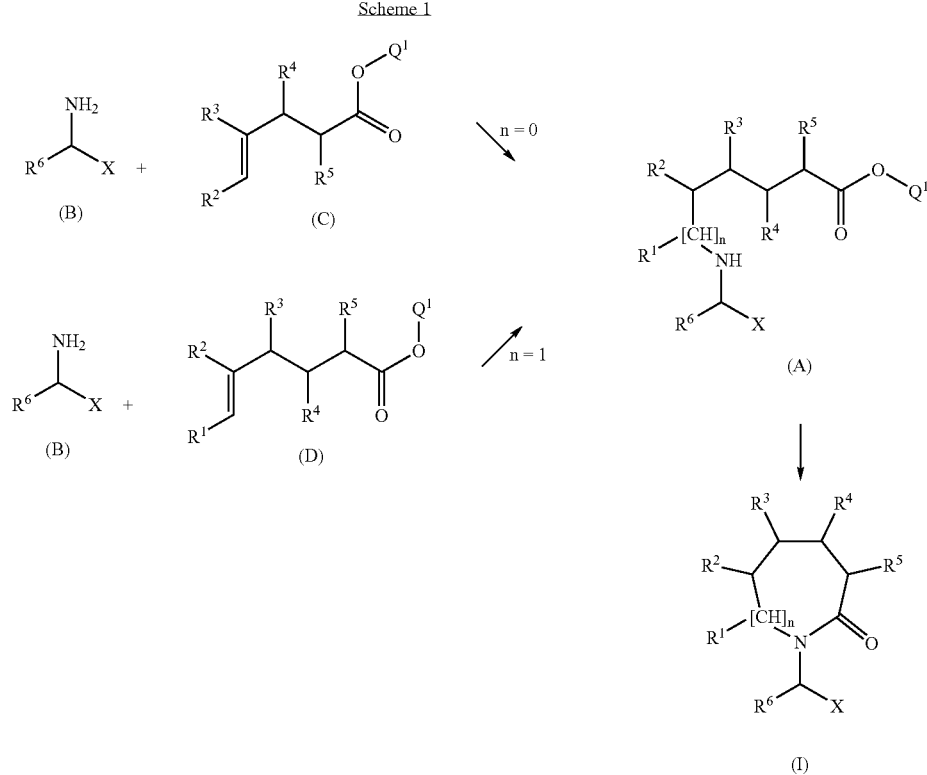

Scheme 1

The first reaction of compound (B) with compound (C) or (D) leading to the formation of the compound of formula (A) is described in: Street, L. J., Baker, R, Book, T., Kneen, C. O., MacLeod, A. M., Merchant, K. J., Showell, G. A., Saunders, J., Herbert, R. H., Freedman, S. B., Harley, E. A., J. Med. Chem. (1990), 33, 2690–2697.

When $Q^1$ represents a methyl or ethyl, the second reaction converting compound of formula (A) into (I) is known by obtained halogenoacid $X^2$=OH). Furthermore, said compound of formula (G) may be prepared by reaction of a compound of formula (J) with an organolithium compound of formula $R^4Li$ in the presence of CuI or, when in formula (G) $R^2$=H, by reduction of a carboxylate of formula (H) wherein $Q^4$ is methyl or ethyl, in the presence of a borohydride reagent. All these reactions are depicted schematically in the following scheme 2.

Scheme 2

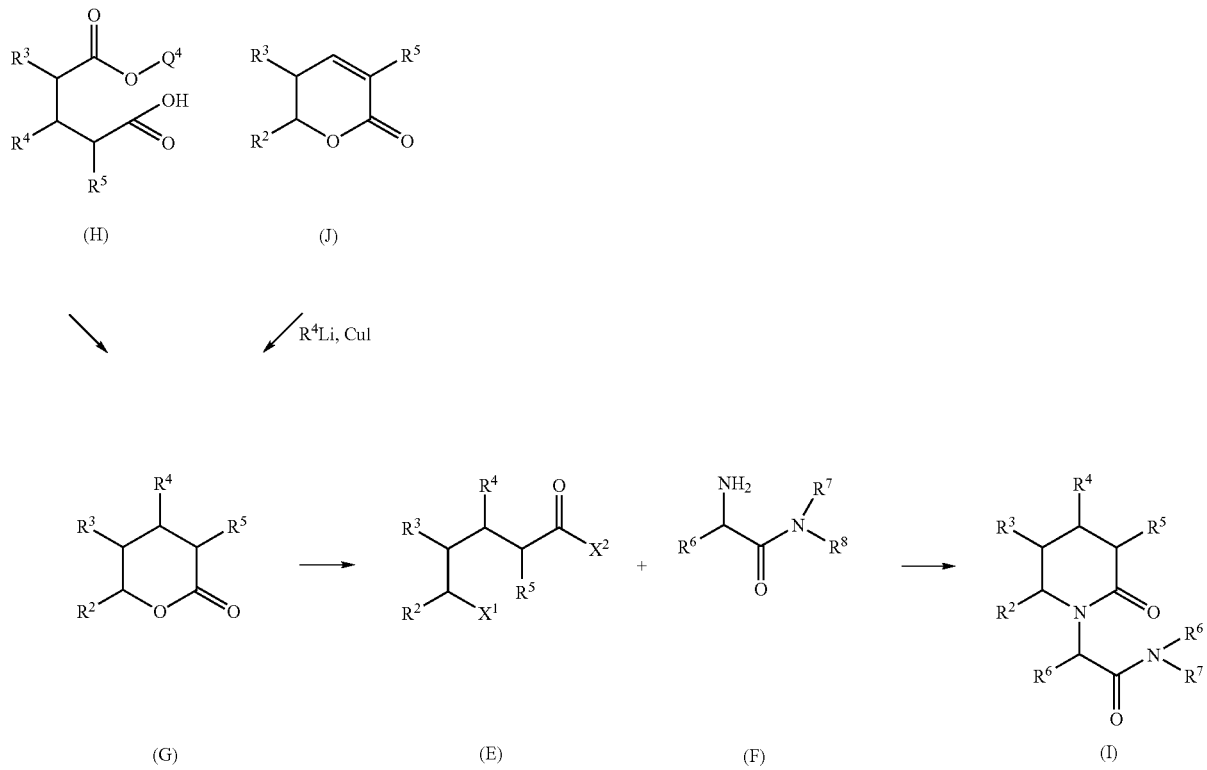

The reaction of the compound of formula (J) with the organolithium compound of formula R⁴Li in the presence of CuI may be carried out according to the procedures described in: Alexakis, A., Berlan, J., Besace, Y., Tetrahedron Lett. (1986), 27, 1047–1050 and in: Lipshutz, B. H., Ellsworth, E. L., Siahaan, T., J. Am. Chem. Soc. (1989), 111, 1351–1358.

Opening of the lactone of formula (G) may be performed according to the procedure described in: Mazzini, C., Lebreton, J., Alphand, V., Furstoss, R., Tetrahedron Lett. (1998), 38, 1195–1196 and in Olah, G. A, Narang, S. C., Gupta, B. G. B., Malhotra, R., J. Org. Chem. (1979), 44, 1247–1250. Halogenation ($X^2$=halogen) or esterification ($X^2$=O$Q^1$) of the obtained haloalkanoic acid ($X^2$=OH) may be performed under any conditions known to the person skilled in the art.

The reaction of a compound of formula (E) with a compound of formula (F) forming compound (I) may be carried out in an inert solvent, for example dichloromethane, at a temperature of about 0° C. in the presence of a phase transfer catalyst, such as tetrabutylammonium bromide in the presence of powdered potassium hydroxide (Patent Application GB 2225322 A).

According to yet another embodiment, compounds of the general formula (I), wherein $A^1$=O and X=—COOR⁹, R⁹ representing an alkyl group, may also be prepared by reaction of a compound of formula (K) wherein M represents an alkali metal, with a compound of formula (L) wherein $X^3$ represents a halogen atom, according to the following scheme 3.

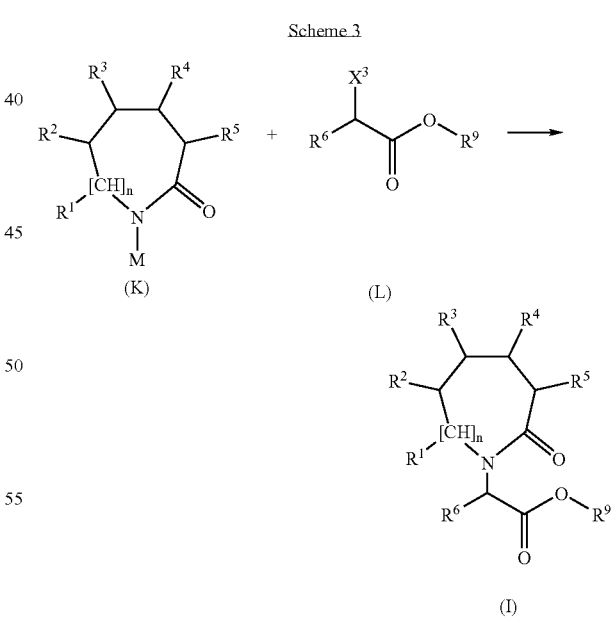

Compounds of formula (K) may be prepared according to the procedure described in: Georg, G., Guan, X., Kant, J., Bioorg. Med. Chem. Lett. (1991), 1, 125.

Alternatively, compounds of formula (K) wherein n=0 may be prepared according to the procedure described in: Koelsch, C. F., J. Am. Chem. Soc. (1943), 65, 2093–2095.

According to yet a further embodiment, the invention relates to a process for preparing a compound of general formula (I), wherein $A^1$=O and X=—$CONR^7R^8$ and none of the groups $R^1$, $R^2$, $R^3$, $R^4$, $R^5$ and $R^6$ being substituted by carboxylic or sulfonic acids or esters or ketone, wherein said process comprises the ammonolysis of the corresponding compound wherein X=—$COOR^9$, $R^9$ being a hydrogen atom or a linear or branched C1–4-alkyl group. Alternatively, transformation into the amino form may be done under conventional peptidic synthesis conditions using coupling agents, for example alkyl chloroformate or dicyclohexylcarbodiimide.

Other processes for preparation of compounds of the general formula (1) and intermediates are known by the man skilled in the art.

For instance, compounds of formula (I) wherein $A^1$=O, X=$CONR^7R^8$, and one of the groups $R^1$, $R^2$, $R^3$, $R^4$, $R^5$ and $R^6$ represents —$G^3$—$COOCH_3$, $G^3$ being a bond or an alkylene group, are key synthesis intermediates for corresponding compounds wherein one of the groups $R^1$, $R^2$, $R^3$, $R^4$, $R^5$ and $R^6$ represents —$G^3$—$CH_2OH$ (March, J., "Advanced Organic Chemistry, Third Edition", John Wiley & Sons, (1985), 1101–1102).

Furthermore, compounds of formula (I) wherein $A^1$=O, X=$CONR^7R^8$, and one of the groups $R^1$, $R^2$, $R^3$, $R^4$, $R^5$ and $R^6$ represents —$G^3$—$CH_2OH$, $G^3$ being a bond or an alkylene group, are key synthesis intermediates for corresponding compounds wherein one of the groups $R^1$, $R^2$, $R^3$, $R^4$, $R^5$ and $R^6$ represents —$G^3$—$CH_2X^3$ or —$G^3$—CHO, wherein $X^3$ represents a chlorine, a bromine or a iodine atom, or a group of formula —O—$SO_2$—$R^{14}$ wherein $R^{14}$ represents an alkyl or an aryl group. These transformations may be performed under any conditions known to the person skilled in the art.

In addition, compounds of formula I wherein $A^1$=0, X=$CONR^7R^8$, and one of the groups $R^1$, $R^2$, $R^3$, $R^4$, $R^5$ and $R^6$ represents —$G^3$—$CH_2OSO_2R^{14}$, $G^3$ being a bond or an alkylene group and $R^{14}$ being a methyl or a tolyl group, are key synthesis intermediates for corresponding compounds wherein one of the groups $R^1$, $R^2$, $R^3$, $R^4$, $R^5$ and $R^6$ represents —$G^3$—$CH_2N_3$ or —$G^3$—$CH_2X^4$, wherein $X^4$ represents an halogen atom. These transformations may be performed under any conditions known to the person skilled in the art.

Finally, compounds of formula I wherein $A^1$=0, X=$CONR^7R^8$, and one of the groups $R^1$, $R^2$, $R^3$, $R^4$, $R^5$ and $R^6$ represents —$G^3$—CHO, $G^3$ being a bond or an alkylene group, are key synthesis intermediates for corresponding compounds wherein one of the groups $R^1$, $R^2$, $R^3$, $R^4$, $R^5$ and $R^6$ represents —$G^3$-$R^{15}$ wherein $R^{15}$ represents a vinyl group not substituted, mono- or di-substituted by halogen atoms or alkyl groups (Wittig type reaction).

According to a last embodiment, the present invention encompasses any of the intermediates prepared by any of the processes described above.

Representative intermediates of this invention as defined above are selected from the group consisting of methyl 1-[(1S)-1-(aminocarbonyl)propyl]-6-oxo-(3S)-3-piperidinecarboxylate and methyl 1-[(1S)-1-(aminocarbonyl)propyl]-6-oxo-(3R)-3-piperidinecarboxylate and their mixtures, (2S)-2-[(5R)-5-(hydroxymethyl)-2-oxo-1-piperidinyl]butanamide and (2S)-2-[(5S)-5-(hydroxymethyl)-2-oxo-1-piperidinyl]butanamide and their mixtures, 1-[(1S)-1-(aminocarbonyl)propyl]-6-oxo-(3R)-3-piperidinyl]methyl methanesulfonate and {1-[(1S)-1-(aminocarbonyl)propyl]-6-oxo-(3S)-3-piperidinyl}methyl methanesulfonate and their mixtures, 5-phenyl-2-piperidinone, ethyl 2-(2-oxo-5-phenyl-1-piperidinyl)butanoate, ethyl 7-oxo-4-azepanecarboxylate, ethyl 1-[1-(tert-butoxycarbonyl)propyl]-7-oxo-4-azepanecarboxylate, 2-[5-(ethoxycarbonyl)-2-oxo-1-azepanyl]butanoic acid, 1-[1-(aminocarbonyl)propyl]-7-oxo-4-azepanecarboxylate, 2-[5-(hydroxymethyl)-2-oxo-1-azepanyl]butanamide.

In the preparation processes according to the invention, the reaction products may be isolated from the reaction medium and, if necessary, further purified according to methodologies generally known in the art such as, for example extraction, crystallization, distillation, trituration and chromatography, or any combination of the same.

When compounds of formula I present one or several stereogenic centres, and that non-stereoselective methods of synthesis are used, resolution of the mixture of stereoisomers can best be effected in one or several steps, involving generally sequential separation of mixtures of diastereomers into their constituting racemates, using preferably chromatographic separations on achiral or chiral phase in reversed or preferably in direct mode, followed by at least one ultimate step of resolution of each racemate into its enantiomers, using most preferably chromatographic separation on chiral phase in reversed or preferably in direct mode. Alternatively, when partly stereoselective methods of synthesis are used, the ultimate step may be a separation of diastereomers using preferably chromatographic separations on achiral or chiral phase in reversed or preferably in direct mode.

Some of the intermediates are known compounds or may be prepared according to art-known procedures.

The present compounds of this invention differ from the art by their structure and by their favourable pharmacological properties. The following examples are provided for illustrative purposes only and are not intended, nor should they be construed, as limiting the invention in any manner. Those skilled in the art will appreciate that routine variations and modifications of the following examples can be made without exceeding the spirit or scope of the invention.

EXAMPLES

Example 1

Analytical Characterization of 6- and 7-ring Compounds

Unless specified otherwise in the examples, characterization of the compounds was performed according to the following methods:

NMR spectra are recorded on a BRUKER AC 250 Fourier Transform NMR Spectrometer fitted with an Aspect 3000 computer and a 5 mm $^1H/^{13}C$ dual probehead or BRUKER DRX 400 FT NMR fitted with a SG Indigo$^2$ computer and a 5 mm inverse geometry $^1H/^{13}C/^{15}N$ triple probehead. The compound is studied in DMSO-$d_6$ (or $CDCl_3$) solution at a probe temperature of 313 K and at concentrations ranging from 2 to 20 mg/ml. The instrument is locked on the deuterium signal of DMSO-$d_6$ (or $CDCl_3$). Chemical shifts are given in ppm downfield from TMS taken as internal standard.

Mass spectrometric measurements in LC/MS mode are performed as follows:

HPLC Conditions

Analyses are performed using a WATERS Alliance HPLC system mounted with an INERTSIL ODS 3-, DP 5 µm, 250×4.6 mm column.

The gradient runs from 100% solvent A (acetonitrile, water, TFA (10/90/0.1, v/v/v)) to 100% solvent B (acetonitrile, water, TFA (90/10/0.1, v/v/v)) in 7 min with a hold at 100% B of 4 min. The flow rate is set at 2.5 ml/min and a split of 1/10 is used just before API source. The chromatography is carried out at 30° C.

MS Conditions

Samples are dissolved in acetonitrile/water, 70/30, v/v at the concentration of about 250 μg/ml. API spectra (+ or −) are performed using a FINNIGAN (San Jose, Calif., USA) LCQ ion trap mass spectrometer. APCI source operates at 450° C. and the capillary heater at 160° C. ESI source operates at 3.5 kV and the capillary heater at 210° C.

Mass spectrometric measurements in EI/DIP mode are performed as follows: samples are vaporized by heating the probe from 50° C. to 250° C. in 5 min. EI (Electron Impact) spectra are recorded using a FINNIGAN (San Jose, Calif., USA) TSQ 700 tandem quadrupole mass spectrometer. The source temperature is set at 150° C.

Specific rotation is recorded on a Perkin-Elmer MC241 or MC341 polarimeter. The angle of rotation is recorded at 25° C. on 1% solutions in MeOH. For some molecules, the solvent is CH$_2$Cl$_2$ or DMSO, due to solubility problems.

Water content is determined using a Metrohm microcoulometric Karl Fischer titrator.

Preparative chromatographic separations are performed on silicagel 60 Merck, particle size 15–40 μm, reference 1.15111.9025, using in-house modified Jobin Yvon-type axial compression columns (80 mm i.d.), flow rates between 70 and 150 ml/min. Amount of silicagel and solvent mixtures are as described in individual procedures.

Preparative chiral chromatographic separations are performed on a DAICEL Chiralpak AD 20 μm, 100*500 mm column using an in-house build instrument with various mixtures of lower alcohols and C$_5$ to C$_8$ linear, branched or cyclic alkanes at ±350 mil/min. Solvent mixtures are as described in individual procedures.

Melting points are determined on a Büchi 535 Totoli-type fusionometre, and are not corrected, or by the onset temperature on a Perkin Elmer DSC 7.

Unless specified otherwise in the examples, the compounds are obtained in the neutral form.

Example 2

Preparation of Intermediates 2.1. Synthesis of methyl 1-[(1S)-1-(aminocarbonyl)propyl]-6-oxo-3-piperidinecarboxylate 1 and 2

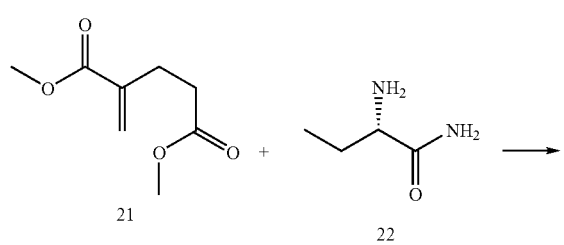

-continued

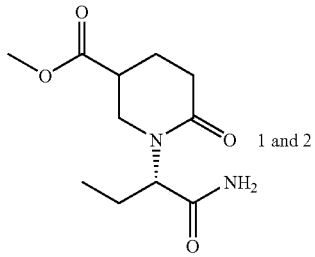

1 and 2

In a 100 ml three necked flask fitted with magnetic stirrer and reflux condenser, under inert atmosphere, 19 g (186 mmoles, 2.66 eq) of (S)-2-aminobutanamide 22 and 12 g (70 mmoles, 1 eq) of dimethyl 2-methylenepentanedioate 21 were dissolved in 50 ml of MeOH. 5 ml of acetic acid were added and the mixture was brought to reflux for 7 days. After cooling down, it was concentrated to dryness, dissolved in CH$_2$Cl$_2$, washed successively with water, 0.5 N HCl and brine, dried over MgSO$_4$ and concentrated to dryness to give 17.8 g of crude amide ester as a mixture of diastereomers. It was purified by PrepLC (1 kg SiO$_2$, CH$_2$Cl$_2$/MeOH/NH$_4$OH, 97.25/2.5/0.25) to give 6.8 g of diastereoisomer 1 (first eluted) and 4.59 g of diastereoisomer 2 (second eluted), 67% yield. Both were recrystallised from ethyl acetate/hexane.

2.2. Synthesis of (2S)-2–[5-(hydroxymethyl)-2-oxo-1-piperidinyl]butanamide 3

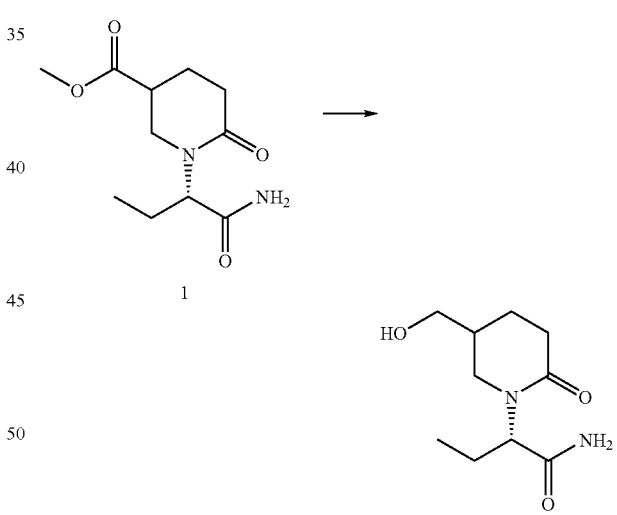

In a 250 ml three necked flask fitted with magnetic stirrer and reflux condenser, under inert atmosphere, 6.29 g (26 mmoles, 1 eq) of methyl 1-[(1S)-1-(aminocarbonyl)propyl]-6-oxo-3-piperidinecarboxylate 1 were dissolved in 35 ml of EtOH and the mixture cooled down to 0° C. 2.5 g (66 mmoles, 9.5 eq) of solid NaBH$_4$ were then added by portions over 1.5 hour, all the while maintaining the temperature around 0° C. After 2 hours, the temperature was raised to 12° C. for 1 hour, and lowered again to 0° C. 10 ml of a saturated solution of NH$_4$Cl were added slowly, followed by 10 ml of acetone, and the mixture was left 1 hour at 0° C. The mixture was filtered, the precipitate washed with 3×10 ml of EtOH and the combined organic fractions concentrated to dryness to give 5.9 g of crude alcohol. It was purified by PrepLC (500 g $SiO_2$, $CH_2Cl_2$/MeOH, 90/10) to give 2.6 g of (2S)-2-[5-(hydroxymethyl)-2-oxo-1-piperidinyl]butanamide 3, (52% yield).

Compound such as (2S)-2-[4-(hydroxymethyl)-2-oxo-1-piperidinyl]butanamide can be synthesized in an analogous way.

2.3. Synthesis of 1-[(1S)-1-(aminocarbonyl)propyl]-6-oxo-3-piperidinyl}methyl methanesulfonate 23

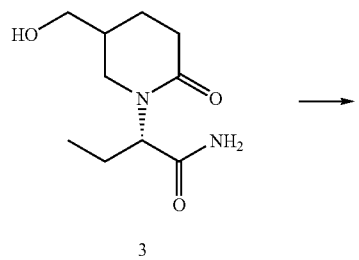

In a 100 ml three necked flask fitted with magnetic stirrer, dropping funnel and reflux condenser under inert atmosphere, 1.9 g (8.8 mmoles, 1 eq) of (2S)-2-[5-(hydroxymethyl)-2-oxo-1-piperidinyl]butanamide 3 were suspended in 50 ml of acetone and cooled down to 0° C. 2.5 ml (17.8 mmoles, 2 eq) of dry triethylamine were added in one portion, followed by dropwise addition of a solution of 0.75 ml (8.8 mmoles, 1 eq) of methanesulfonyl chloride in 5 ml of acetone, all the while maintaining the temperature below 4° C. After 3 hours, the mixture was filtered, the residue washed with acetone and the combined organic phases concentrated to dryness to give 3.4 g of crude 1-[(1S)-1-(aminocarbonyl)propyl]-6-oxo-3-piperidinyl methyl methanesulfonate. It was purified by PrepLC (400 g $SiO_2$, $CH_2Cl_2$/MeOH, 96/4) to give 1.4 g of pure methanesulfonate 23, (62% yield).

Compound such as {1-[(1S)-1-(aminocarbonyl)propyl]-2-oxo-4-piperidinyl}methyl methanesulfonate 24 can be synthesized in an analogous way.

Example 3

Synthesis of (2S)-2-[5-(azidomethyl)-2-oxo-1-piperidinyl]butanamide 7

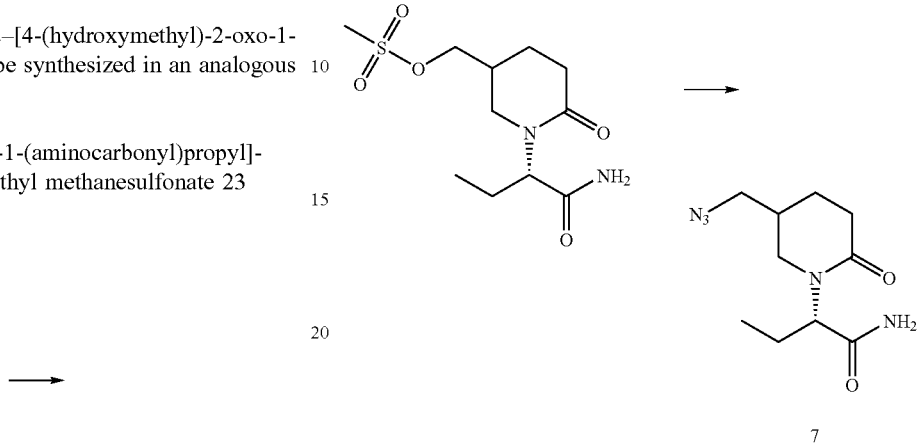

In a 50 ml three necked flask fitted with magnetic stirrer and reflux condenser, under inert atmosphere, 1.4 g (5.1 mmoles, 1 eq) of 1-[(1S)-1-(aminocarbonyl)propyl]-6-oxo-3-piperidinyl}methyl methanesulfonate 23 were dissolved in 15 ml of DMF. 400 mg (6.15 mmoles, 1.2 eq) of solid sodium azide were added in one portion, and the mixture was heated up to 80° C. for 1 hour. The DMF was evaporated in vacuum, the residue suspended in $CH_2Cl_2$ and the precipitate filtered off. The filtrate was concentrated to dryness to give 1 g of crude material. It was purified by PrepLC (200 g $SiO_2$, $CH_2Cl_2$/MeOH, 97/3) to give 500 mg of pure azide 7, 45% yield.

Example 4

Synthesis of (2S)-2-[4-(iodomethyl)-2-oxo-1-piperidinyl]butanamide 13

In a 150 ml three necked flask fitted with magnetic stirrer and reflux condenser, under inert atmosphere, 6.88 g (23.5 nmoles) of {1-[(1S)-1-(aminocarbonyl)propyl]-6-oxo-3-piperidinyl}methyl methanesulfonate 24 were dissolved in 86 ml of THF. 3.9 g (25.9 mmoles, 1.1 eq) of sodium iodide were added in one portion and the mixture was brought to reflux. After 5 hours, 780 mg (5.2 mmoles, 0.22 eq) of sodium iodide were added and reflux continued for a total of 10 hours. After cooling down to 0° C., the mixture was filtered, the precipitate washed with THF, the combined organic fractions concentrated to dryness and purified by PrepLC (800 g $SiO_2$, $CH_2Cl_2$/MeOH, 95/5) to give 7.21 g of crude compound. It was crystallised from 80 ml ethanol to give 5 g of pure iodide 13, 66% yield.

Example 5

Preparation of Ethyl 2-(2-oxo-5-phenyl-1-piperidinyl)butanoate 26

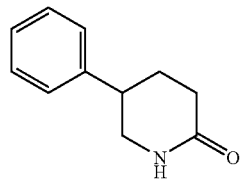

25

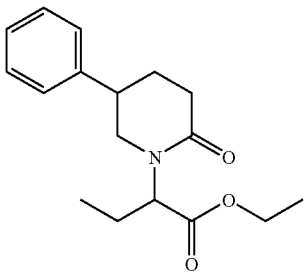

26

Synthesis of the 5-phenyl-2-piperidinone 25: Koelsch, J. Amer. Chem. Soc. (1943), 65, 2093; the racemate was resolved by Chiral PrepLC (Chiralpak AD, petroleum ether/isopropanol, 90/10, 20° C.).

In a 1 l three necked flask fitted with reflux condenser, magnetic stirrer and dropping funnel under inert atmosphere, 9.8 g (87 mmoles) of potassium t-butoxide were suspended in 600 ml of dry toluene. 11.8 g (67 mmoles) of 5-phenyl-2-piperidinone 25 were added, and the mixture stirred for 30 min. 17 g (87 mmoles) of ethyl 2-bromobutanoate were added and the temperature raised to 70° C. for 5 hours. 600 ml of ethyl acetate were added, the solution was washed twice with brine, the organic phase dried over magnesium sulfate, filtered and concentrated to dryness. The residue was purified by PrepLC (1 kg $SiO_2$, $CH_2Cl_2$/EtOH, 97.5/2.5) to give 3.7 g of pure ester 26 as a mixture of diastereomers, 70.4% yield.

Compound such as methyl 1-[1-(aminocarbonyl)propyl]-2-oxo-4-piperidinecarboxylate can be synthesized in an analogous way.

Example 6

Preparation of 2-(2-oxo-5-phenyl-1-piperidinyl)butanamide 9, 10, 11 and 12

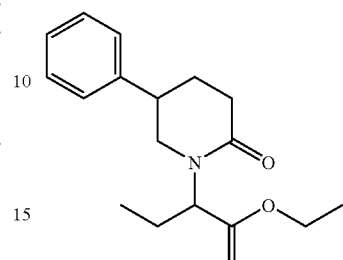

26

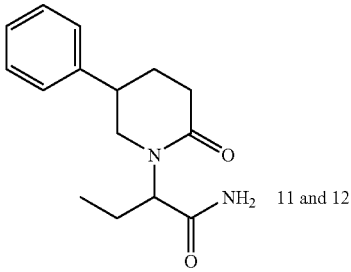

11 and 12

In a 1 l three necked flask fitted with reflux condenser, magnetic stirrer and a gas inlet tube dipping in the solution, 13.6 g (47 mmoles) of ethyl 2-(2-oxo-5-phenyl-1-piperidinyl)butanoate 26 were dissolved in 800 ml of methanol containing 22 mg of dissolved sodium. Gaseous ammonia was bubbled through the solution, and the saturated solution kept at room temperature for 3 days, while occasionally resaturating with ammonia. After completion of the reaction, the solution was concentrated to dryness. The residue was purified by PrepLC (1 kg $SiO_2$, $CH_2Cl_2$/MeOH, 95/5) to give 10.1 g of butanamide. The diastereoisomers were then separated (Chiralpak AD, ethanol) to give 4.5 g of diastereoisomer 11 (first eluted) and 4.3 g of diastereoisomer 12 (second eluted) (72%). Both were recrystallised from ethanol.

Example 7

Method for Preparation of 7-Ring Compounds

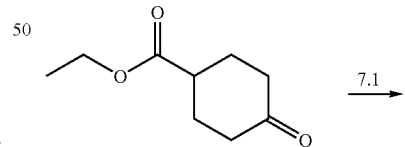

27

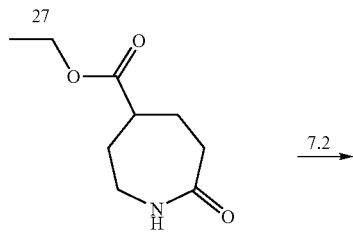

28

-continued

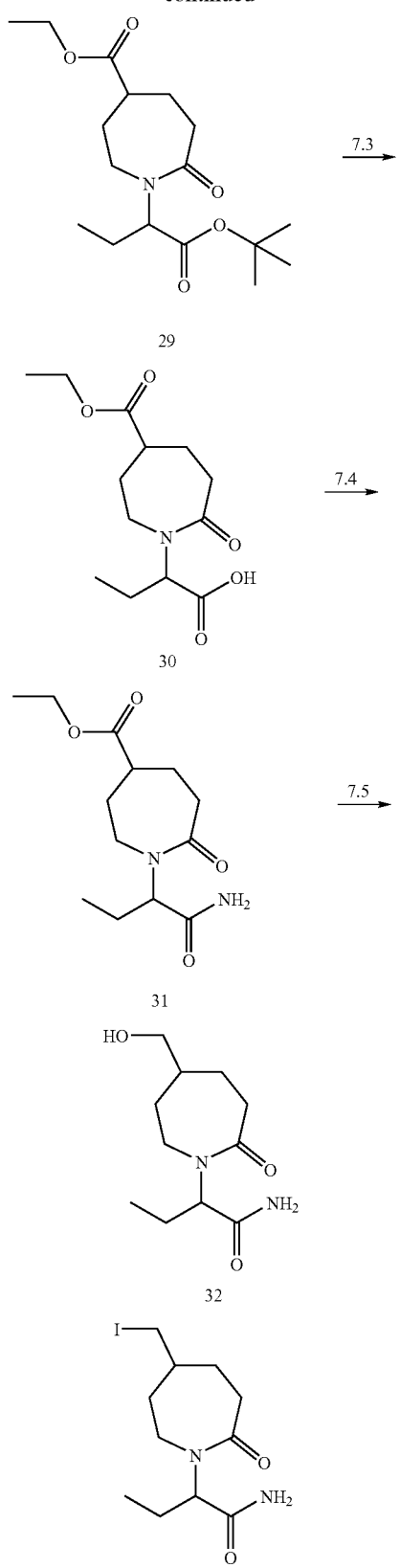

29

30

31

32

17, 18, 19 & 20

7.1. Preparation of ethyl 7-oxo-4-azepanecarboxylate 28

In a 250 ml three necked flask fitted with reflux condenser, magnetic stirrer and dropping funnel under inert atmosphere, 5.6 ml (5.98 g, 34 mmoles, 1 eq) of ethyl 4-oxocyclohexanecarboxylate 27 were dissolved in 50 ml of $CHCl_3$. 6.65 g (102 mmole, 3 eq) of sodium azide were added, followed by 22.1 ml (32.8 g, 341 mmoles, 10 eq) of methanesulfonic acid dissolved in 20 ml of over 30 min. The mixture was heated to reflux for 1 hour and cooled down to 10° C. 200 nl of saturated sodium bicarbonate solution were added, the mixture decanted and the aqueous phase extracted with 3×150 ml of $CHCl_3$, the combined organic phases were dried over magnesium sulfate, filtered and concentrated to dryness. The residue was purified by PrepLC (800 g $SiO_2$, $CH_2Cl_2$/MeOH, 97/3) to give 5.1 g of crude compound. It was crystallised from 40 ml of diethylether to give 4.41 g of pure ester 28, 70% yield.

7.2. Preparation of ethyl 1-[1-(tert-butoxycarbonyl) propyl]-7-oxo-4-azepanecarboxylate 29

In a 150 ml three necked flask fitted with reflux condenser, magnetic stirrer and dropping funnel under inert atmosphere, 5.09 g (27.5 mmoles, 1 eq) of ethyl 7-oxo-4-azepanecarboxylate 28 and 12.27 g (55 mmoles, 2 eq) of tert-butyl 2-bromobutanoate were dissolved in 70 ml of acetonitrile. The temperature was raised to 50° C. and 1.32 g (55 mmoles, 2 eq) of sodium hydride were added portionwise (exothermic). The mixture was stirred one more hour at 50° C. and concentrated to dryness, the residue was poured on ice/water and neutralised with solid ammonium chloride. The mixture was extracted three times with $CH_2Cl_2$, the combined organic phases were dried over magnesium sulfate, filtered and concentrated to dryness. The residue was purified by PrepLC (1 kg $SiO_2$, $CH_2Cl_2$/MTBE, 85/15) to give 8.5 g of pure diester 29, 69% yield.

7.3. Preparation of 2-[5-(ethoxycarbonyl)-2-oxo-1-azepanyl]butanoic Acid 30

In a 25 ml three necked flask fitted with magnetic stirrer and dropping funnel under inert atmosphere, 1 g (3.1 mmoles) of pure ethyl 1-[1-(tert-butoxycarbonyl)propyl]-7-oxo-4-azepanecarboxylate 29 was dissolved in 5 ml of $CH_2Cl_2$. The mixture was cooled down to 0° C., 5 ml of trifluoroacetic acid was added. The mixture was kept at 0° C. under stirring for 24 hours, concentrated to dryness and used as such in the next step.

7.4. Preparation of Ethyl 1-[1-(aminocarbonyl)propyl]-7-oxo-4-azepanecarboxylate 31

In a 250 ml three necked flask fitted with reflux condenser, magnetic stirrer and dropping funnel under inert atmosphere, 5.48 g (20.2 mmoles, 1 eq) of 2–[5-(ethoxycarbonyl)-2-oxo-1-azepanyl]butanoic acid 30 were dissolved in 150 ml of ethyl acetate, and 7.44 g (40.4 mmoles, 2 eq) of pentafluorophenol and 8.34 g (40.4 mmoles, 2 eq) of dicyclohexycarbodiimide were added, and the mixture kept under stirring at room temperature for 4 hours. 1.86 g of pentafluorophenol and 2.08 g of dicyclohexycarbodiimide (10.7 mmoles, 0.5 eq each) were added, and stirring continued for 1 hour. The mixture was filtered, the residue washed with ethyl acetate, and the combined organic phases concentrated to dryness. The residue was taken up in 160 ml of $CH_2Cl_2$, cooled down to 0° C., saturated with gaseous ammonia and stirred at that temperature for 6 hours with occasional resaturations. The mixture was filtered, the residue washed with $CH_2Cl_2$, and the combined organic phases concentrated to dryness. The residue was purified and separated into diastereomers by PrepLC (1 kg $SiO_2$, $CH_2Cl_2$/i-PrOH/$NH_4OH$, 92.5/7/0.5), to give 2.33 g of the first eluted diastereoisomer (racemate) and 2.7 g of the second diastereomer (racemate), 92% total yield.

Steps 7.5. and 7.6. were described in the previous examples (2.2, 2.3 and 4).

Compounds with other ring substituents than iodine, or with substituents at other positions on the ring structure can be synthesized in an analogous way.

Example 8

Characterization of the Interactions Between a Test Substance and LBS

LBS stands for Levetiracetam Binding Site, it is an unknown component of brain tissue that has been shown to bind levetiracetam (M. Noyer et al., Eur. J. Pharmacol. (1995), 286, 137–146).

The inhibition constant ($K_i$) of a compound is determined in competitive binding experiments by measuring the binding of a single concentration of a radioactive ligand at equilibrium with various concentrations of the unlabeled test substance. The concentration of the test substance inhibiting 50% of the specific binding of the radioligand is called the $IC_{50}$. The equilibrium dissociation constant $K_i$ is proportional to the $IC_{50}$ and is calculated using the equation of Cheng and Prusoff (Cheng Y. et al., Biochem. Pharmacol. (1972), 22, 3099–3108).

The concentration range usually encompasses 6 log units with variable steps (0.3 to 1 log). Assays are performed in mono- or duplicate, each $K_i$ determination is performed on two different samples of test substance. Cerebral cortex from 200–250 g male Sprague-Dawley rats were homogenised using a Potter S homogeniser (10 strokes at 1,000 rpm; Braun, Germany) in 20 mmol/l Tris-HCl (pH 7.4), 250 mmol/l sucrose (buffer A); all operations were performed at 4° C. The homogenate was centrifuged at 30,000 g for 15 min. The crude membrane pellet obtained was resuspended in 50 mmol/l Tris-HCl (pH 7.4), (buffer B) and incubated 15 min at 37° C., centrifuged at 30,000 g for 15 min and washed twice with the same buffer. The final pellet was resuspended in buffer A at a protein concentration ranging from 15 to 25 mg/ml and stored in liquid nitrogen.

Membranes (150–200 μg of protein/assay) are incubated at 4° C. for 120 min in 0.5 ml of a 50 mmol/l Tris-HCl buffer (pH 7.4) containing 2 mmol/l $MgCl_2$, 1 to 2.10–9 mol/l of [$^3$H]-2-[4-(3-azidophenyl)-2-oxo-1-pyrrolidinyl]butanamide (levetiracetam analog, a tritiated radioligand currently used for the labelling of LBS), and increasing concentrations of the test substance. The non specific binding (NSB) is defined as the residual binding observed in the presence of a concentration of reference substance (e.g. $10^{-3}$ mol/l levetiracetam) that binds essentially all the receptors. Membrane-bound and free radioligands are separated by rapid filtration through glass fiber filters (equivalent to Whatman GF/C or GF/B; VEL, Belgium) pre-soaked in 0.1% polyethyleneimine and $10^{-3}$ mol/l levetiracetam to reduce non specific binding. Samples and filters are rinsed by at least 6 ml of 50 mmol/l Tris-HCl (pH 7.4) buffer. The entire filtration procedure does not exceed 10 seconds per sample.

The radioactivity trapped onto the filters is counted by liquid scintillation in a β-counter Tri-Carb 1900 or TopCount 9206, Camberra Packard, Belgium, or any other equivalent counter). Data analysis is perfomed by a computerized non linear curve fitting method using a set of equations describing several binding models assuming populations of independent non-interacting receptors which obey to the law of mass. In tables I-A and I-B the $pK_i$ values of various 4- or 5-substituted 2-oxo-1-piperidinyl and 5-substituted 2-oxo-1-azepanyl butanamide compounds are compared to the activity of the non-substituted levetiracetam, with a $PK_i$ of 6.1±0.1. The lower the $K_i$ (the higher the $pK_i$), the stronger the binding, and thus generally the more potent the ligand (the drug).

Example 9

Animal Model of Sound-susceptible Mice

The objective of this test is to evaluate the anticonvulsant potency of a compound in sound-susceptible mice, a genetic animal model with reflex seizures. In this model of primary generalised epilepsy, seizures are evoked without electrical or chemical stimulation and the seizure types are, at least in part, similar in their clinical phenomenology to seizures occurring in man (Löscher W. & Schmidt D., Epilepsy Res. (1998), 2, 145–181; Buchhalter J. R., Epilepsia (1993), 34, S31–S41).

Male or female genetically sound-sensitive mice (14–28 g; N=10), derived from a DBA strain originally selected by Dr. Lehmann of the Laboratory of Acoustic Physiology (Paris) and bred in the UCB Pharma Sector husbandry unit since 1978, were used. The experimental design consisted of several groups, one group receiving the vehicle control and the other groups different doses of the test-compound. The compounds were administered intraperitoneally 60 minutes before the induction of audiogenic seizures. The range of the doses administered had a logarithmic progression, generally between $1.0 \times 10^{-5}$ mol/kg and $1.0 \times 10^{-3}$ mol/kg, but lower or higher doses were tested if necessary.

For testing, the animals were placed in small cages, one mouse per cage, in a sound-attenuated chamber. After a period of orientation of 30 seconds, the acoustic stimulus (90 dB, 10–20 kHz) was delivered for 30 seconds via loudspeakers positioned above each cage. During this interval, the mice were observed and the presence of the 3 phases of the seizure activity namely wild running, clonic and tonic convulsions, was recorded. The proportion of mice protected against wild running, clonic and tonic convulsions, respectively, was calculated.

For active compounds, an $ED_{50}$ value, i.e. the dose (expressed in moles per kg of test animal) producing 50% protection relative to the control group, together with 95% confidence limits, was calculated using a Probit Analysis (SAS/STAT® Software, version 6.09, PROBIT procedure) of the proportions of protected mice for each of the 3 phases of the seizure activity.

In tables I-A and I-B the $ED_{50}$ value (=AUD CC) for the inhibition of Clonic Convulsions in the Audiogenic seizure test are given. This test is a good animal model for the screening of anticonvulsant and/or antiepileptic compounds. Our reference compound is levetiracetam, with a $ED_{50}$ CC of 180 μmol/kg. The lower the $ED_{50}$ the more potent the compound.

In the table, the stereochemical information is contained in the two columns headed 'configuration data'. The second column indicates whether a compound has no stereogenic center (ACHIRAL), is a pure enantiomer (PURE), a racemate (RAC) or is a mixture of two or more stereoisomers, possibly in unequal proportions (MIXT). The first column contains the stereochemical assignment for each recognised center, following the IUPAC numbering used in the preceding column. A number alone indicates the existence of both configurations at that center. A number followed by 'R' or 'S' indicates the known absolute configuration at that center. A number followed by '§' indicates the existence of only one but unknown absolute configuration at that center. The letter (A, B, C, D) in front is a way of distinguishing the various enantiomers or racemates of the same structure.

In the tables, the melting points are in most cases determined by the onset of the DSC curve. When a visual (fusionometer) melting point is given, the value is in parenthesis.

TABLE I

Synthesis intermediates

| | IUPAC NAME | Configuration | Mp (° C.) | LC/MS MH+ | $^1$H NMR |
|---|---|---|---|---|---|
| 1 | Methyl 1-[(1S)-1-(aminocarbonyl)propyl]-6-oxo-3-piperidinecarboxylate | A-1S, 3§ | PURE | (64–65) | | |
| 2 | Methyl 1-[(1S)-1-(aminocarbonyl)propyl]-6-oxo-3-piperidinecarboxylate | B-1S, 3§ | PURE | (98–100) | | |
| 3 | (2S)-2-[5-(hydroxymethyl)-2-oxo-1-piperidinyl]butanamide | A-2S, 5§ | PURE | (138–141) | | |
| 4 | (2S)-2-[5-(hydroxymethyl)-2-oxo-1-piperidinyl]butanamide | B-2S, 5§ | PURE | (142–143) | | |
| 23 | 1-[(1S)-1-(aminocarbonyl)propyl]-6-oxo-3-piperidinyl}methyl methanesulfonate | A-2S, 5§ | PURE | | | [1] |
| 24 | {1-[(1S)-1-(aminocarbonyl)propyl]-6-oxo-3-piperidinyl}methyl methanesulfonate | A-2S, 5§ | PURE | | | [2] |
| 25 | 5-phenyl-2-piperidinone | A-5§ | PURE | | | [3] |
| 26 | Ethyl 2-(2-oxo-5-phenyl-1-piperidinyl)butanoate | A-2, 4§ | MIXT | | | [4] |
| 28 | Ethyl 7-oxo-4-azepanecarboxylate | 5 | RAC | | 186 | |
| 29 | Ethyl 1-[1-(tert-butoxycarbonyl)propyl]-7-oxo-4-azepanecarboxylate | 2, 5 | MIXT | | 328 | |
| 30 | 2-[5-(ethoxycarbonyl)-2-oxo-1-azepanyl]butanoic acid | 2, 5 | MIXT | | 272 | |
| 31 | 1-[1-(aminocarbonyl)propyl]-7-oxo-4-azepanecarboxylate | 2, 5 | MIXT | | 271 | |
| 32 | 2-[5-(hydroxymethyl)-2-oxo-1-azepanyl]butanamide | A-2, 5 | RAC | | 229 | |

TABLE II $^1$H NMR description

| $^1$H NMR Number | $^1$H NMR Description | Solvent |
|---|---|---|
| [1] | 0.79(t, 3H), 1.47–1.68(m, 2H), 1.75–1.93(m, 2H), 2.12–2.40(m, 3H), 3.09(dd, 1H), 3.18(s, 3H), 3.24(dd, 1H), 4.20(d, 2H), 4.84(dd, 1H), 6.90(broad s, 1H), 7.15(broad s, 1H) | DMSO |
| [2] | 0.81(t, 3H), 1.49–1.65(m, 2H), 1.81–1.91(m, 2H), 2.09–2.44(m, 3H), 3.11(dd, 1H), 3.18(s, 3H), 3.27–3.38(m, 1H), 4.12(d, 2H), 4.82(dd, 1H), 6.92(broad s, 1H), 7.1(broad s, 1H) | DMSO |
| [3] | 1.91–2.04(m, 2H), 2.20–2.40(m, 2H), 2.92–3.04(m, 1H), 3.17–3.33(m, 2H), 7.19–7.32(m, 5H), 7.45(broad s, 1H) | DMSO |
| [4] | 0.87 and 0.88(2t, 3H), 1.19 and 1.20(2t, 3H), 1.69–2.05(m, 4H), 2.42–2.49 (m, 2H), 3.07–3.13(m, 1H), 3.27–3.35(m, 2H), 4.10(q, 1H), 4.75–4.87 (2dd, 1H), 7.23–7.35(m, 5H) | DMSO |

TABLE III A 6-ring compounds

| | IUPAC NAME | Configuration | | Mp | PKi | AUD CC |
|---|---|---|---|---|---|---|
| 5 | (2S)-2-[5-(iodomethyl)-2-oxo-1-piperidinyl]butanamide | A-2S, 5§ | PURE | 100.6 | ++ | 1.6E–04 |
| 6 | (2S)-2-[5-(iodomethyl)-2-oxo-1-piperidinyl]butanamide | B-2S, 5§ | PURE | 60.2 | +++ | 2.0E–04 |
| 7 | (2S)-2-[5-(azidomethyl)-2-oxo-1-piperidinyl]butanamide | A-2S, 5§ | PURE | 70.1 | +++ | 1.2E–04 |

TABLE III A-continued 6-ring compounds

| | IUPAC NAME | Configuration | | Mp | PKi | AUD CC |
|---|---|---|---|---|---|---|
| 8 | (2S)-2-[5-(azidomethyl)-2-oxo-1-piperidinyl]butanamide | B-2§, 5§ | PURE | 96.6 | ++ | 2.8E−04 |
| 9 | 2-(2-oxo-5-phenyl-1-piperidinyl)butanamide | A-2§, 5§ | PURE | 167.0 | | 2.8E−04 |
| 10 | 2-(2-oxo-5-phenyl-1-piperidinyl)butanamide | B-2§, 5§ | PURE | 160.7 | | Inactive |
| 11 | 2-(2-oxo-5-phenyl-1-piperidinyl)butanamide | C-2§, 5§ | PURE | 158.9 | +++ | 7.0E−05 |
| 12 | 2-(2-oxo-5-phenyl-1-piperidinyl)butanamide | D-2§, 5§ | PURE | 167.8 | | Inactive |
| 13 | (2S)-2-[4-(iodomethyl)-2-oxo-1-piperidinyl]butanamide | A-2S, 4§ | PURE | 144.0 | +++ | 1.1E−04 |
| 14 | (2R)-2-[4-(iodomethyl)-2-oxo-1-piperidinyl]butanamide | B-2R, 4§ | PURE | 144.3 | | Inactive |
| 15 | (2S)-2-[4-(iodomethyl)-2-oxo-1-piperidinyl]butanamide | B-2S, 4§ | PURE | 153.7 | +++ | 2.5E−04 |
| 16 | (2R)-2-[4-(iodomethyl)-2-oxo-1-piperidinyl]butanamide | A-2S, 4§ | PURE | 153.3 | | Inactive |

TABLE III B 7-ring compounds

| | IUPAC NAME | Configuration | | Mp | LC/MS MH+ | pKi | AUD CC |
|---|---|---|---|---|---|---|---|
| 17 | 2-[5-(iodomethyl)-2-oxo-1-azepanyl]butanamide | A-2§, 5§ | PURE | | 339 | + | |
| 18 | 2-[5-(iodomethyl)-2-oxo-1-azepanyl]butanamide | B-2§, 5§ | PURE | | 339 | +++ | 1.3E−04 |
| 19 | 2-[5-(iodomethyl)-2-oxo-1-azepanyl]butanamide | C-2§, 5§ | PURE | 111.7 | | + | Inactive |
| 20 | 2-[5-(iodomethyl)-2-oxo-1-azepanyl]butanamide | D-2§, 5§ | PURE | 111.2 | | ++ | 5.6E−04 |

Legend
+ = pKi < 5.5
++ = 5.5 ≦ pKi < 6.5
+++ = 6.5 ≦ pKi < 7.5
++++ = pKi ≧ 7.5
inactive = inactive at 1.0E−03

What is claimed is:

1. Compounds of the formula I

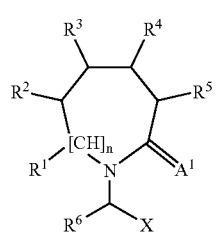

(I)

wherein
n is equal to 1;
$A^1$ is an oxygen atom;
X is —$CONR^7R^8$;
$R^1$, $R^2$ and $R^5$ are hydrogen
$R^3$ and $R^4$ are the same or different and each is independently hydrogen, ester of formula —CO—O—$R^{11}$, alkyl optionally substituted by one or more substituents selected from halogen and hydroxy, alkenyl optionally substituted by one or more halogen, alkynyl optionally substituted by one or more halogen, or aryl optionally substituted by one or more halogen,
provided that at least one of $R^3$ and $R^4$ is not hydrogen;
$R^6$ is hydrogen or alkyl;
$R^7$ and $R^8$ are the same or different and each is independently hydrogen or alkyl;
$R^{11}$ is alkyl; and
their pharmaceutically acceptable salts, geometrical isomers, enantiomers, diastereoisomers and mixtures thereof, and all possible mixtures of stereoisomers.

2. The compound according to claim 1 wherein X is —$CONH_2$.

3. The compound according to claim 1 wherein $R^6$ is hydrogen or a $C_{1-4}$ alkyl.

4. The compound according to claim 1 wherein $R^6$ is a $C_{1-4}$ alkyl.

5. The compound according to claim 4 wherein $R^6$ is ethyl.

6. A compound according to claim 1 wherein the carbon atom to which $R^6$ is attached is of the S configuration.

7. A compound according to claim 1 wherein $R^3$ and $R^4$ are the same or different and each is independently hydrogen;

$C_{1-12}$ alkyl, each optionally substituted by one or more substituents selected from hydroxy and halogen;

$C_{2-12}$ alkenyl, each optionally substituted by one or more halogen;

$C_{2-12}$ alkynyl, each optionally substituted by one or more halogen; and ester of formula —CO—O—$R^{11}$ wherein $R^{11}$ is $C_{1-12}$ alkyl.

8. A compound according to claim 1, wherein $R^3$ and $R^4$ are the same or different and each is independently hydrogen;

$C_{1-7}$ alkyl, each optionally substituted by one or more substituents selected from hydroxy and halogen;

$C_{2-6}$ alkenyl, each optionally substituted by one or more halogen;

$C_{2-6}$ alkynyl, each optionally substituted by one or more halogen; and phenyl, each optionally substituted by one or more halogen.

9. A compound according to claim 1 wherein at least one of $R^3$ and $R^4$ is independently $C_{1-4}$ alkyl or $C_{3-7}$ cycloalkyl, optionally substituted by one or more hydroxy or halogen.

10. A compound according to claim 1 wherein at least one of $R^3$ and $R^4$ is independently vinyl, optionally substituted by one or more halogen.

11. A compound according to claim 1 wherein at least one of $R^3$ and $R^4$ is independently ethynyl, propynyl or butynyl, optionally substituted by one or more halogen.

12. A compound according to claim 1 wherein at least one of $R^3$ and $R^4$ is independently phenyl, optionally substituted by one or more halogen.

13. A compound according to claim 1 wherein $R^4$ is hydrogen.

14. A compound according to claim 1 wherein $R^3$ is hydrogen.

15. A compound according to claim 1 selected from the group consisting of 2-[5-(hydroxymethyl)-2-oxo-1-azepanyl]butanamide, 2-(2-oxo-5-propyl-1-azepanyl)butanamide, 2-[2-oxo-5-(3,3,3-trifluoropropyl)-1-azepanyl]butanamide, 2-[5-(cyclopropylmethyl)-2-oxo-1-azepanyl]butanamide, 2-[5-(iodomethyl)-2-oxo-1-azepanyl]butanamide, 2-(2-oxo-5-phenyl-1-azepanyl)butanamide, 2-[5-(3-chlorophenyl)-2-oxo-1-azepanyl]butanamide, 2-[5-(2,2-difluorovinyl)-2-oxo-1-azepanyl]butanamide, 2-[5-(2,2-dibromovinyl)-2-oxo-1-azepanyl]butanamide, 2-[5-(2,2-dichlorovinyl)-2-oxo-1-azepanyl]butanamide, 2-(5-ethynyl-2-oxo-1-azepanyl)butanamide, 2-[2-oxo-5-(3,3,3-trifluoro-1-propynyl)-1-azepanyl]butanamide, 2-[2-oxo-5-(1-propynyl)-1-azepanyl]butanamide, 2-[5-(cyclopropylethynyl)-2-oxo-1-azepanyl]butanamide, 2-[5-(3-methyl-1-butynyl)-2-oxo-1-azepanyl]butanamide, 2-[5-(1-butynyl)-2-oxo-1-azepanyl]butanamide, 2-[5-(2,2-difluoropropyl)-2-oxo-1-azepanyl]butanamide, 2-[5-(2-chloro-2,2-difluoroethyl)-2-oxo-1-azepanyl]butanamide, 2-[5-(2-bromo-2,2-difluoroethyl)-2-oxo-1-azepanyl]butanamide, 2-[5-(2,2,2-trifluoroethyl)-2-oxo-1-azepanyl]butanamide, 2-[4-(hydroxymethyl)-2-oxo-1-azepanyl]butanamide, 2-(2-oxo-4-propyl-1-azepanyl)butanamide, 2-[2-oxo-4-(3,3,3-trifluoropropyl)-1-azepanyl]butanamide, 2-[4-(cyclopropylmethyl)-2-oxo-1-azepanyl]butanamide, 2-[4-(iodomethyl)-2-oxo-1-azepanyl]butanamide, 2-(2-oxo-4-phenyl-1-azepanyl)butanamide, 2-[4-(3-chlorophenyl)-2-oxo-1-azepanyl]butanamide, 2-[4-(2,2-difluorovinyl)-2-oxo-1-azepanyl]butanamide, 2-[4-(2,2-dibromovinyl)-2-oxo-1-azepanyl]butanamide, 2-[4-(2,2-dichlorovinyl)-2-oxo-1-azepanyl]butanamide, 2-(4-ethynyl-2-oxo-1-azepanyl)butanamide, 2-[2-oxo-4-(3,3,3-trifluoro-1-propynyl)-1-azepanyl]butanamide, 2-[2-oxo-4-(1-propynyl)-1-azepanyl]butanamide, 2-[4-(cyclopropylethynyl)-2-oxo-1-azepanyl]butanamide, 2-[4-(3-methyl-1-butynyl)-2-oxo-1-azepanyl]butanamide, 2-[4-(1-butynyl)-2-oxo-1-azepanyl]butanamide, 2-[4-(2,2-difluoropropyl)-2-oxo-1-azepanyl]butanamide, 2-[4-(2-chloro-2,2-difluoroethyl)-2-oxo-1-azepanyl]butanamide, 2-[4-(2-bromo-2,2-difluoroethyl)-2-oxo-1-azepanyl]butanamide, 2-[4-(2,2,2-trifluoroethyl)-2-oxo-1-azepanyl]butanamide.

16. The compound according to claim 1 which is 2-[5-(iodomethyl)-2-oxo-1-azepanyl]butanamide.

17. The compound according to claim 16 which is a pure enantiomer.

18. A pharmaceutical composition comprising as active ingredient a therapeutically effective amount of a compound according to claim 1 and a pharmaceutically acceptable adjuvant, diluent or carrier.

19. A pharmaceutical composition comprising as active ingredient a therapeutically effective amount of a compound according to claim 15 and a pharmaceutically acceptable adjuvant, diluent or carrier.

20. A pharmaceutical composition comprising as active ingredient a therapeutically effective amount of a compound according to claim 16 and a pharmaceutically acceptable adjuvant, diluent or carrier.

21. A method for treating epilepsy, epileptogenesis, seizure disorders and convulsions, in a mammal in need of such treatment, comprising administering a therapeutic dose of at least one compound according to claim 1.

* * * * *

UNITED STATES PATENT AND TRADEMARK OFFICE
CERTIFICATE OF CORRECTION

PATENT NO. : 7,087,596 B2  Page 1 of 1
APPLICATION NO. : 10/476791
DATED : August 8, 2006
INVENTOR(S) : Philippe Michel et al.

It is certified that error appears in the above-identified patent and that said Letters Patent is hereby corrected as shown below:

On Title Page (item 22)
On the first page of the Letters Patent the PCT filing date should read May 17, 2002 instead of May 17, 2003.

Signed and Sealed this

Fourteenth Day of November, 2006

JON W. DUDAS
*Director of the United States Patent and Trademark Office*